(12) United States Patent
Kota

(10) Patent No.: US 10,801,025 B2
(45) Date of Patent: Oct. 13, 2020

(54) MICRORNA THERAPY FOR PANCREATIC CANCER

(71) Applicant: Indiana University Research and Technology Corporation, Indianapolis, IN (US)

(72) Inventor: Janaiah Kota, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/660,403

(22) Filed: Jul. 26, 2017

(65) Prior Publication Data

US 2018/0030442 A1 Feb. 1, 2018

Related U.S. Application Data

(60) Provisional application No. 62/366,887, filed on Jul. 26, 2016.

(51) Int. Cl.
*C12N 15/113* (2010.01)
*A61K 31/713* (2006.01)
*A61K 45/06* (2006.01)

(52) U.S. Cl.
CPC .......... *C12N 15/113* (2013.01); *A61K 31/713* (2013.01); *A61K 45/06* (2013.01); *C12N 2310/141* (2013.01); *C12N 2320/31* (2013.01)

(58) Field of Classification Search
CPC ...... A61K 45/06; A61K 48/00; C12N 15/111; C12N 15/113; C12N 2310/141
USPC ............ 424/174.1; 435/6.1, 6.11, 6.12, 6.14, 435/91.1, 91.31, 455; 514/44; 536/23.1
See application file for complete search history.

(56) References Cited

U.S. PATENT DOCUMENTS

| | | |
|---|---|---|
| 8,247,389 B2 | 8/2012 | Gay et al. |
| 8,530,159 B2 | 9/2013 | Croce |
| 8,618,073 B2 | 12/2013 | Deshmukh et al. |
| 8,951,983 B2 | 2/2015 | Hornstein et al. |
| 9,017,940 B2 | 4/2015 | Croce et al. |
| 9,376,681 B2 | 6/2016 | Montgomery et al. |
| 2012/0251619 A1 | 10/2012 | Gunaratne |
| 2014/0322553 A1 | 10/2014 | Foley et al. |
| 2015/0031749 A1 | 1/2015 | Simmons |
| 2015/0094357 A1 | 4/2015 | Croce |
| 2017/0218454 A1* | 8/2017 | Plaisier ............... C12Q 1/6886 |
| 2018/0230546 A1* | 8/2018 | Ahlquist ............. C12N 15/113 |

OTHER PUBLICATIONS

Kwon et al, Scientific Reports, vol. 5: 11450, pp. 1-15 (Year: 2015).*
Xu et al, Amer. J. Pathology, vol. 177, No. 5, pp. 2585-2596 (Year: 2010).*
Hwang et al, Cancer Res., vol. 68, No. 3, pp. 918-926 (Year: 2008).*
Hruban et al., Pancreatic Intraepithelial Neoplasia: A new Nomenclature and Classification System for Pancreatic Duct Lesions; The American Journal of Surgical Pathology: May 2001; vol. 25, No. 5, pp. 579-586.
Kwon et al., Pathophysiological Role of microRNA-29 in Pancreatic Cancer Stroma, Scientific Reports 5, Article No. 11450 (Jun. 2015).
Zou, Y., et al., miR-29c suppresses pancreatic cancer liver metastasis in an orthotopic implantation model in nude mice and affects survival in pancreatic cancer patients. Carcinogenesis, 2015. 36(6): p. 676-84.
Trehoux, S., et al., Micro-RNAs miR-29a and miR-330-5p function as tumor suppressors by targeting the MUC1 mucin in pancreatic cancer cells. Biochim Biophys Acta, 2015. 1853(10 Pt A): p. 2392-403.
Mott, J.L., et al., mir-29 regulates Mcl-1 protein expression and apoptosis. Oncogene, 2007. 26(42): p. 6133-40.
Noetel, A., et al., microRNA are Central Players in Anti- and Profibrotic Gene Regulation during Liver Fibrosis. Front Physiol, 2012. 3: p. 49.
Justus, Calvin R. et al., "In vitro Cell Migration and Invasion Assays", Journal of Visualized Experiments, Jun. 1, 2014.
Matrisian, Lynn M., PhD, MBA et al., "The Past, Present, and Future of Pancreatic Cancer Clinical Trials", American Society of Clinical Oncology, 2016.

* cited by examiner

*Primary Examiner* — Jane J Zara
(74) *Attorney, Agent, or Firm* — Faegre Drinker Biddle & Reath LLP

(57) ABSTRACT

Methods for inhibiting pancreatic cancer cell migration and invasion are disclosed herein. Further, methods for inhibiting autophagy are disclosed. More particularly, as discussed herein, increasing miR-29 expression in the tumor microenvironment inhibits migration, invasion and autophagy in cancer patients.

9 Claims, 28 Drawing Sheets
(9 of 28 Drawing Sheet(s) Filed in Color)
Specification includes a Sequence Listing.

|  | Seed | |
|---|---|---|
| 29a | 5' uagcaccauucugaaaucgguua- 3' | (SEQ ID NO:1) |
| 29b | 5' uagcaccauuugaaaucaguguu- 3' | (SEQ ID NO:2) |
| 29c | 5' uagcaccauuugaaaucgguua- 3' | (SEQ ID NO:3) |

TFEB
| | | | | |
|---|---|---|---|---|
| Hsa 3' | A—C—UU | UGGUGCUA | AUAGC-UC 5' | (SEQ ID NO:4) |
| Ptr 3' | A—C—UU | UGGUGCUA | AUAGC-UC 5' | (SEQ ID NO:5) |
| Mmu 3' | C—A—UU | UGGUGCUA | AUAGC-UC 5' | (SEQ ID NO:6) |
| Rno 3' | C—A—UU | UGGUGCUA | AUAGC-UC 5' | (SEQ ID NO:7) |
| Ocu 3' | A—C—UU | UGGUGCUA | AUAGC-UC 5' | (SEQ ID NO:8) |
| Laf 3' | A—C—UU | UGGUGCUA | AUAGC-UC 5' | (SEQ ID NO:9) |
| | | AGCUCCAA | | TFEB Mut |

ATG9A
| | | | | |
|---|---|---|---|---|
| Hsa 3' | GGUCAAAGA | UCGUGGUG | UGUGAGA 5' | (SEQ ID NO:10) |
| Ptr 3' | GGUCAAAGA | UCGUGGUG | UGUGAGA 5' | (SEQ ID NO:11) |
| Mmu 3' | GGUCAAAGA | UCGUGGUG | UGUGAGA 5' | (SEQ ID NO:12) |
| Rno 3' | GGUCAAAGA | UCGUGGUG | UGUGAGA 5' | (SEQ ID NO:13) |
| Cpo 3' | GGUCAAAGA | UCGUGGUG | UGUGAGA 5' | (SEQ ID NO:14) |
| Dno 3' | GGUCAAAGA | UCGUGGUG | UGUGAGA 5' | (SEQ ID NO:15) |
| | | UCGUGGUG | | ATG9A Mut |

Conserved 3' UTR binding Site

FIG. 4A

SEQUENCE LISTING

```
<160> NUMBER OF SEQ ID NOS: 15

<210> SEQ ID NO 1
<211> LENGTH: 22
<212> TYPE: RNA
<213> ORGANISM: Artificial Sequence
<220> FEATURE:
<223> OTHER INFORMATION: Synthetic

<400> SEQUENCE: 1
uagcaccauc ugaaaucggu ua                                            22

<210> SEQ ID NO 2
<211> LENGTH: 23
<212> TYPE: RNA
<213> ORGANISM: Artificial Sequence
<220> FEATURE:
<223> OTHER INFORMATION: Synthetic

<400> SEQUENCE: 2
uagcaccauu ugaaaucagu guu                                           23

<210> SEQ ID NO 3
<211> LENGTH: 22
<212> TYPE: RNA
<213> ORGANISM: Artificial Sequence
<220> FEATURE:
<223> OTHER INFORMATION: Synthetic

<400> SEQUENCE: 3
uagcaccauu ugaaaucggu ua                                            22

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
acuuuggugc uaauagcuc                                                19

<210> SEQ ID NO 5
<211> LENGTH: 19
<212> TYPE: RNA
<213> ORGANISM: Artificial Sequence
```

```
<220> FEATURE:
<223> OTHER INFORMATION: Synthetic

<400> SEQUENCE: 5 acuuggugc uaauagcuc                                                  19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6 cauuggugc uaauagcuc                                                  19

<210> SEQ ID NO 7
<211> LENGTH: 19
<212> TYPE: RNA
<213> ORGANISM: Artificial Sequence
<220> FEATURE:
<223> OTHER INFORMATION: Synthetic

<400> SEQUENCE: 7 cauuggugc uaauagcuc                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8 acuuggugc uaauagcuc                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9 acuuggugc uaauagcuc                                                  19

<210> SEQ ID NO 10
<211> LENGTH: 24
<212> TYPE: RNA
<213> ORGANISM: Artificial Sequence
<220> FEATURE:
<223> OTHER INFORMATION: Synthetic

<400> SEQUENCE: 10
ggucaaagau cguggugugu gaga                                           24

<210> SEQ ID NO 11
<211> LENGTH: 24
<212> TYPE: RNA
<213> ORGANISM: Artificial Sequence
<220> FEATURE:
<223> OTHER INFORMATION: Synthetic

<400> SEQUENCE: 11
ggucaaagau cguggugugu gaga                                           24
```

```
<210> SEQ ID NO 12
<211> LENGTH: 24
<212> TYPE: RNA
<213> ORGANISM: Artificial Sequence
<220> FEATURE:
<223> OTHER INFORMATION: Synthetic

<400> SEQUENCE: 12
ggucaaagau cguggugugu gaga                                              24

<210> SEQ ID NO 13
<211> LENGTH: 24
<212> TYPE: RNA
<213> ORGANISM: Artificial Sequence
<220> FEATURE:
<223> OTHER INFORMATION: Synthetic

<400> SEQUENCE: 13
ggucaaagau cguggugugu gaga                                              24

<210> SEQ ID NO 14
<211> LENGTH: 24
<212> TYPE: RNA
<213> ORGANISM: Artificial Sequence
<220> FEATURE:
<223> OTHER INFORMATION: Synthetic

<400> SEQUENCE: 14
ggucaaagau cguggugugu gaga                                              24

<210> SEQ ID NO 15
<211> LENGTH: 24
<212> TYPE: RNA
<213> ORGANISM: Artificial Sequence
<220> FEATURE:
<223> OTHER INFORMATION: Synthetic

<400> SEQUENCE: 15
ggucaaagau cguggugugu gaga                                              24
```

MICRORNA THERAPY FOR PANCREATIC CANCER

CROSS-REFERENCE TO RELATED APPLICATIONS

This application claims priority to U.S. Provisional Application Ser. No. 62/366,887 filed on Jul. 26, 2016, the entire disclosure of which is incorporated herein by reference in its entirety.

STATEMENT IN SUPPORT FOR FILING A SEQUENCE LISTING

A paper copy of the Sequence Listing and a computer readable form of the Sequence Listing containing the file named "IURTC_2016_149_02_5 T25.txt", which is 3,022 bytes in size (as measured in MICROSOFT WINDOWS EXPLORER), are provided herein and are herein incorporated by reference. This Sequence Listing consists of SEQ ID NOs:1-15.

BACKGROUND OF THE DISCLOSURE

The present disclosure relates generally to the treatment of cancer, and particularly, pancreatic cancer, by increasing expression of miR-29 in the tumor microenvironment. Particularly, overexpression of miR-29 has been found to inhibit cancer cell migration, invasion, and autophagy.

The pancreas is the primary site of origin for a wide variety of diseases including pancreatic ductal adenocarcinoma (PDAC). PDAC is one of the most lethal forms of human malignancies in the world. Pancreatic cancer remains the third leading cause of cancer death in the United States, with an annual mortality nearly equivalent to the annual incidence. PDAC has a high resistance to chemo- and radiation therapy, including intrinsic and acquired chemoresistant behaviors by cancer cells. The most commonly used chemotherapy for pancreatic cancer is gemcitabine. Gemcitabine has a modest clinical benefit and may not improve overall survival to a meaningful degree. Further, although combination chemotherapies such as Nab-Paclitaxel/Gemcitabine and FOLFIRINOX modestly improves survival, the overall 5-year survival rate has not exceeded 8% for the last 30 years. Therefore, understanding the underlying mechanisms of drug resistance in pancreatic cancer is critical to develop new, effective treatments.

Autophagy is the process in which cells degrade internal constituents for the maintenance of cellular homeostasis and survival under stress conditions. Recent studies document that the upregulation of autophagy can serve as a survival mechanism in various malignancies, including PDAC tumor growth and progression. These reports have paved the way for clinical trials utilizing hydroxychloroquine (HCQ), a lysosomotropic agent, in PDAC patients to inhibit autophagy as a means of therapy. However, HCQ is associated with toxicity and off-target effects such as neuromyotoxicity, retinopathy, and cardiomyopathy.

Increasing evidence suggests that microRNA (miRNA)-based therapeutics have limited off-target effects and could emerge as novel therapeutic agents for various human diseases including cancer. Specifically restored expression of downregulated miRNAs has been suggested to be beneficial in cancer therapies. Studies have shown downregulation of miR-29 in PDAC.

The human miR-29 family of microRNAs has three mature members, miR-29a, miR-29b, and miR-29c. Strong antifibrotic effects of miR-29s have been demonstrated in heart, kidney, and other organs. miR-29s have also been shown to be proapoptotic and involved in the regulation of cell differentiation. Overexpression of miR-29 in stromal cells reduced the accumulation of stromal proteins and cancer colony formation in direct co-cultures.

Based on the foregoing, there is an unmet need for more efficient treatments to overcome chemotherapeutic resistance in pancreatic cancer. One such strategy proposed herein for the method of treating cancer, and in particular PDAC, is to increase the levels of miR-29 in the cancer cells. Particularly, by administering isolated miR-29 or a miR-29 mimic to a subject having cancer such as PDAC, it has been found that cancer cell migration, invasion, and/or autophagy are inhibited. Further, regulating the levels of miR-29 in cancer cells weakens the cell attachment proteins, allowing for chemotherapy, such as gemcitabine, to reach the tumor cells. This increases the cytotoxicity of the chemotherapy, providing a more effective method of treatment for PDAC.

BRIEF DESCRIPTION OF THE DISCLOSURE

The present disclosure is generally related to inhibiting cancer cell migration, invasion and autophagy in cancer patients. Increasing the expression of miR-29 has been shown to increase the effectiveness of treatment for cancers such as Pancreatic Ductal Adenocarcinoma (PDAC). Particularly, increased expression of miR-29 was shown to inhibit tumor migration and invasion, and to inhibit cancer cell autophagy.

In one aspect, the present disclosure is directed to a method of inhibiting cancer cell migration. The method comprises increasing expression levels of miR-29 in a subject in need thereof.

In another aspect, the present disclosure is directed to a method of inhibiting cancer cell invasion. The method comprises increasing expression levels of miR-29 in a subject in need thereof.

In another aspect, the present disclosure is directed to a method of inhibiting autophagy. The method comprises increasing expression levels of miR-29 in a subject in need thereof. In one particular aspect, it was found that increasing the expression of miR-29 inhibits autophagy by inhibiting late state autophagy. In another particular aspect, it was found that increasing the expression of miR-29 inhibits autophagy by blocking autophagosome-lysosome fusion.

In yet another aspect, the present disclosure is directed to a method of decreasing expression of an autophagy protein selected from transcription factor EB (TFEB), autophagy-related protein 9A (ATG9A), and combinations thereof. The method comprises increasing expression levels of miR-29 in a subject in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

(FIG. 1A) qPCR analysis of miR-29 family members in normal human ductal epithelial cell lines (HPNE and HPDE) and pancreatic cancer cell lines (Panc-1, MIA PaCa-2, COLO 357, BxPC-3, AsPC-1) (N=4). Data represented as average fold change ($^{\Delta\Delta}$CT)±standard error of the mean (S.E.M.) (FIG. 1B) Pancreatic cancer cell lines (Panc-1 and MIA PaCa-2) were seeded into 96-well plates, transfected with control (CTRL) or miR-29a mimics, treated with indicated concentrations of gemcitabine (GEM) for 24 hours post-transfection, and viability was measured at 72 hours post-treatment using the Cell Counting Kit-8 (CCK-8). Average absorbance (A450) is represented (N=8) ±S.E.M. (FIG. 1C) Panc-1 cells were transfected with CTRL or miR-29a mimics, treated with 10 µM GEM for 48 hours and lactate dehydrogenase (LDH) release was determined by substrate based activity assay (fluorescence 560/590 nm). Average relative percent cytotoxicity are represented (N=3-4)±S.E.M. (FIG. 1D) Panc-1 cells were transfected with CTRL or miR-29a mimics 24 hours post-transfection cells were treated with 10 µM GEM for 24 hours, lysed, and caspase activity was determined by absorbance using Apo-ONE Homogeneous Caspase-3/7 Assay according to manufacturer's protocol. Average relative fluorescence (RFU, 490/530 nm) are represented (N=4)±S.E.M. (FIG. 1E) Panc-1 transfected with CTRL or miR-29a mimics, treated with 10 µM GEM for 12 hours and 15 µg of total cell protein lysate was subjected to western blot analysis for procaspase 3, cleaved caspase 3, and GAPDH was used as loading control. Relative quantification of band intensities normalized to GAPDH are shown below respective blots.

(FIG. 2A) Panc-1 cells were transfected with CTRL or miR-29a mimics Following transfection, cells were treated with 25 µM Chloroquine (CQ) and 5 µg of total cell lysates were subjected to western blot analysis for p62 and LC3B, and GAPDH was used as loading control. Relative quantification of band intensities normalized to GAPDH are shown below respective blots. (FIG. 2B) Panc-1 cells were transfected with CTRL or miR-29a mimics and treated with and without 10 µM GEM. In parallel, Panc-1 cells were treated with 10 µM GEM alone or in combination with 10 µM BafA1. 48 hours post GEM treatment, viability was determined using CCK-8 assay kit. Average relative absorbance (A450) normalized to respective controls is presented (N=6)±S.E.M.

(FIG. 3A) Panc-1 stably expressing GFP-LC3B were transfected with CTRL or miR-29a mimics Following transfection, cells were treated with 25 µM CQ. Cells were fixed and stained for lysosomal-associated membrane protein 2 (LAMP-2). (FIG. 3B) Image analysis was conducted to quantify number of GFP-LC3B positive compartments per cell, and averages are presented ±S.E.M. (FIG. 3C) Colocalization was calculated based on GFP-LC3B and LAMP-2 staining, and average percentage of colocalization is presented ±S.E.M.

FIGS. 4A-4D: (FIG. 4A) Schematic representation of the miR-29 family members and 3'-UTR binding sites of miR-29 targets as well as mutated binding sites used in Luciferase Assays: Transcription Factor EB (TFEB) and Autophagy-related protein 9A (ATG9A). All three miR-29 family members (miR-29a, miR-29b, and miR-29c) have identical seed sequences. Conserved miR-29 binding sites in the 3'-UTR of mRNA transcripts encoding ATG9A and TFEB are depicted in bold. (FIG. 4B) 10 µg of total protein cell lysates from Panc-1 transfected with CTRL or miR-29a mimics were subjected to western blot analysis for TFEB, ATG9A, and GAPDH. Relative quantification of band intensities normalized to GAPDH are shown below respective blots. (FIG. 4C) Relative firefly luciferase activity from TFEB and ATG9A 3' UTR wild type (WT) and mutant (mut) reporter constructs following cotransfection into Panc-1 cells with control or miR-29a mimics. All readouts were normalized to *renilla* luciferase activity for each well. Average relative luminesce normalized to respective controls is presented (N=6) ±S.E.M. (FIG. 4D) 5 µg of total protein cell lysates from Panc-1 cells were transfected with CTRL, miR-29a mimics, siCTRL, siTFEB, or siATG9A. 24 hours post-transfection, total protein was harvested and subjected to western blot analysis for p62 and LC3B, and GAPDH was used as loading control. Relative quantification of band intensities normalized to GAPDH relative to respective controls and are shown below respective blots.

(FIG. 5A) Panc-1 cells stably expressing GFP-LC3B were transfected with either CTRL or miR-29a mimics in parallel to cells transfected with siCTRL, siTFEB, or siATG9A. Following transfection, cells were fixed and stained for lysosomal-associated membrane protein 2 (LAMP-2). (FIG. 5B) Image analysis was conducted to quantify number of GFP-LC3B positive compartments per cell, and averages are presented ±S.E.M. (FIG. 5C) Colocalization was calculated based on GFP-LC3B and LAMP-2 staining, and average percentage of colocalization is presented ±S.E.M.

(FIG. 6C) 10 µg of total cell lysates from Panc-1 transfected with CTRL or miR-29a mimics were subjected to western blot analysis for epithelial marker, E-cadherin, and mesenchymal marker, and Vimentin. GAPDH was used as loading control for the analysis. Relative quantification of band intensities normalized to GAPDH are shown below respective blots. (FIG. 6D) Panc-1 cells were transfected with CTRL or miR-29a mimics and plated into soft agar assays. Data presented as average number of colonies per well (N=6)±S.E.M. and representative images are shown below each graph.

(FIG. 8A) Schematic diagram of scAAV.GFP vector. (FIG. 8B) Quantification of GFP expression in C57BL/6 mice administered with $1\times10^{12}$ vg/animal of scAAV8.GFP and scAAV9.GFP via tail vein injection (n=3/group) as determined by percentage GFP+ acinar cells. Representative image of global pancreatic GFP expression shown below each graph column. (FIG. 8C) Quantification of GFP expression in C57BL/6 mice administered with scAAV9.GFP at various doses via tail vein injection (n=3/group) as determined by percentage GFP+ acinar cells. (FIG. 8D) Representative global pancreatic GFP expression of C57BL/6 mice dosed with $5\times10^{12}$ vg scAAV9.GFP at 3 week post-vector administration. Scale bar 0.88 pm, 20× magnification. Data represents mean+Standard Error of the Mean (S.E.M.), *p<0.05.

(FIG. 9A) Uniform Evans blue dye delivery to the entire pancreas via retrograde intraductal infusion procedure. (FIG. 9B) C57BL/6 mouse was dosed with 1×10¹¹ vg of scAAV6.GFP via retrograde intraductal infusion and pancreatic GFP expression was observed via direct fluoresce. (FIGS. 9C & 9D) A cohort of C57BL/6 mice were dosed with scAAV6.GFP, -8, or -9 at 1×10¹¹ vg/animal (n=3-4/group). 3 weeks post-vector infusion, mice were sacrificed, and GFP expression was determined via fluorescence microscopy. Summary graph of GFP+ expression from each group. (FIG. 9C) acinar cells and (FIG. 9D) ductal cells are presented with representative images. Scale bar 0.43 pm, 20× magnification. (FIG. 9E) Cohort of C57BL/6 mice were intraductally infused with different doses of scAAV6.GFP (n=4-6/group), and percentage GFP+ acinar cells was determined. Data represents mean+S.E.M., *p<0.05.

(FIG. 10A) Pancreatic and liver GFP+ expression was determined via florescence microscopy. Representative pancreatic and liver images are shown for each serotype, 20× magnification. (FIG. 10B) Quantification of pancreatic gene expression was determined by percentage GFP+ acinar cells. (FIG. 10C) DNA was isolated from pancreata and liver of scAAV6.GFP or scAAV9.GFP retrograde intraductally infused C57BL/6 mice and subjected to qPCR analysis for AAV genome copy numbers. Data represents mean+S.E.M., *p<0.05. (FIG. 10D) Quantification of pancreatic GFP expression was determined in male and female of C57BL/6 mice dosed with 5×10¹¹ vg of scAAV6 or scAAV9.GFP.

(FIG. 12C) Representative H&E, Trichrome, and B220 images are shown. Scale bar 200 pm, 20× magnification. (FIG. 12D) Representative fat lymphoid response observed at early time points are shown (1-3 days) (H&E). Scale bar 200 pm, 20× magnification. (FIG. 12E) Mean Sirius red or trichrome positive area (%) of pancreatic tissue in retrograde pancreatic intraductally injected C57BL/6 (1-14 days post-injection) mice (n=3-4 mice/time point). Data represents mean±S.E.M. n.s: non-significant.

DETAILED DESCRIPTION

Figure 1A:
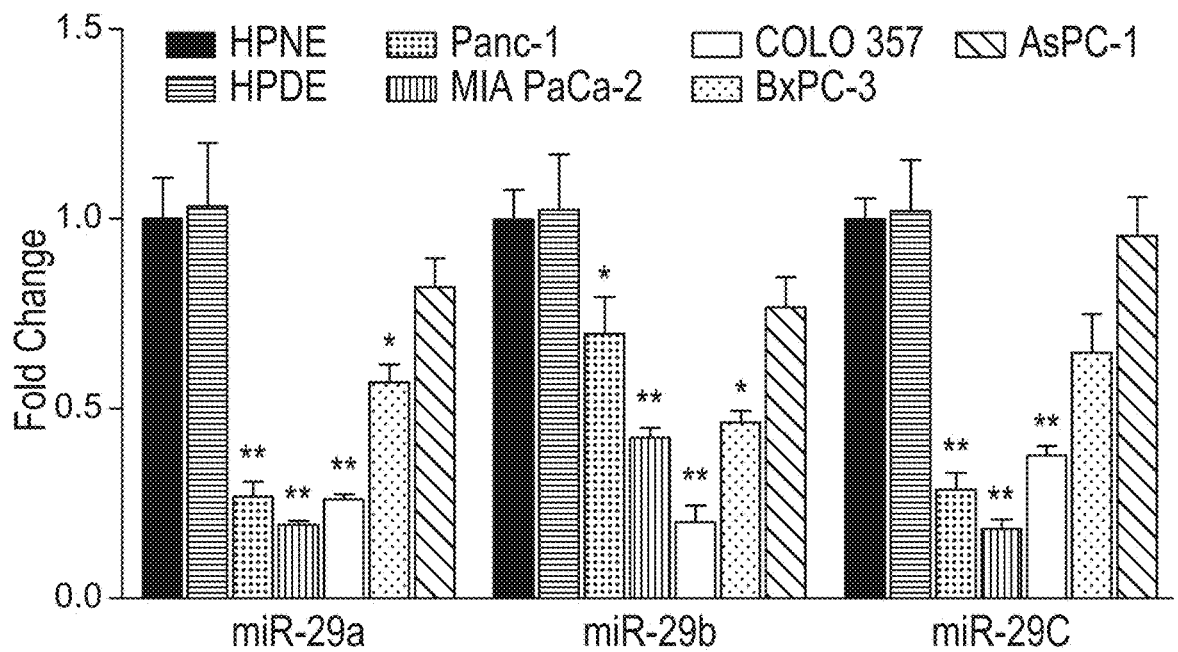
FIGS. 1A-1E.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The methods of the present disclosure are generally related to methods of inhibiting the migration and/or invasion of cancer cells by increasing the levels of miR-29 expression in subjects in need thereof. Strong antifibrotic effects of miR-29s have been demonstrated in heart, kidney, and other organs. miR-29s have also been shown to be proapoptotic and involved in the regulation of cell differentiation.

As used herein, "subjects in need thereof" refers to a subset of subjects in need of increasing expression of miR-29, including increasing the expression of miR-29a, miR-29b, and/or miR-29c. In one embodiment, subjects that are in specific need may include subjects who are susceptible to, or at elevated risk of, diagnosed as suffering from cancer, and in particular, pancreatic cancer, breast cancer, colorectal cancer, prostate cancer, liver cancer, brain cancer, and melanoma. Subjects may be susceptible to, or at elevated risk of, diagnosed due to family history, age, environment, and/or lifestyle.

The methods of the present disclosure generally include increasing miR-29 expression in a subject in need thereof. miR-29 expression can be increased through administration of miR-29 mimics More particularly, synthetic miR-29 mimics can be administered via transient transfection, viral vectors (e.g., Adeno Associated virus or lentivirus), and the like as known in the art. In another particularly suitable embodiment, synthetic miR-29 mimics are encapsulated and administered using liposomal nanoparticles.

Any miR-29 mimics known in the art are suitable for use herein. Exemplary miR-29a mimics include, for example, C-300504-07 (available from GE Dharmacon) and hsa-miR-29a (available from Sigma-Aldrich), as well as miR-29 mimics available from GenePharma. Exemplary miR-29b mimics include, for example, C-300521-05 (available from GE Dharmacon) and has-miR-29b-3 (available from Sigma-Aldrich). Exemplary miR-29c mimics include, for example, C-300650-07 (available from GE Dharmacon) and has-miR-29c-3 (available from Sigma-Aldrich).

Typically, miR-29 mimics can be administered systemically via intravenous delivery or targeted delivery to the primary tumors via intraductal delivery. In another embodiment, miR-29 mimics are administered via direct intratumoral injection. In one particularly suitable embodiment, the miR-29 mimics can be administered using adeno-associated virus (AAV) vectors.

Generally, for use in the methods of the present disclosure the physiological expression levels of miR-29 should be equal to or greater than those levels in epithelial cells of a normal, healthy subject. As used herein, "normal" or "healthy" subject refers to an individual that is not showing symptoms and/or has not be diagnosed with cancer, and in particular, pancreatic cancer, breast cancer, colorectal cancer, prostate cancer, liver cancer, brain cancer, and melanoma. In one particularly suitable embodiment, to inhibit cancer cell migration and invasion, from about 10 nM to about 20 nM of miR-29 mimic is administered to the subject in need thereof.

In another suitable embodiment, expression of miR-29 is increased by manipulation of the pathway leading to miR-29 expression using methods as known to one skilled in the art.

It has been shown that miR-29 is downregulated in other kinds of cancer, such as: breast, colorectal, prostate, liver, brain, melanoma, as well as pancreatic. Increasing the expression of miR-29 in any of these cancers has now been found to inhibit migration and/or invasion of these cancer cells.

As used herein "migration" and "invasion" are used to refer to cell movement throughout a subject's body. "Migration" is the movement of cancer cells from one location to another or one part of the body to another part of the body. "Invasion" is related to migration, and more particularly defines the ability of cells to become motile and navigate through the extracellular matrix within a tissue or to infiltrate neighboring tissues. Cancer cells that become invasive may disseminate to secondary sites and form metastases.

Increasing the level of miR-29 expression in the cells is further been found to be synergistically effective at increasing the sensitivity of the cancer cells to chemotherapeutic treatments. Because of this, inhibiting tumor migration and invasion is done efficiently by using a combination of miR-29 and chemotherapeutic agent, for example, gemcitabine, nab-paclitaxel, FOLFIRINOX, and combinations thereof. In one particular embodiment, the methods include administering gemcitabine with miR-29 to increase the sensitivity of the cancer cells to chemotherapeutic treatments.

When used in combination with miR-29, dosages of the additional chemotherapeutic agents will depend on the type of chemotherapeutic agent, other agents being used in combination with miR-29 and the chemotherapeutic agent, age and weight of the subject to be treated, as well as the severity of the cancer to be treated. Typically, when administered with miR-29, gemcitabine is administered in dosages ranging from about 500 mg/m$^2$ to about 1000 mg/m$^2$. When administered with miR-29, nab-paclitaxel is administered in dosages ranging from about 100 mg/m$^2$ to about 250 mg/m$^2$. And, when administered with miR-29, FOLFIRINOX is administered as follows: 5-fluorouracil (FU), from about 250 mg/m$^2$ to about 2000 mg/m$^2$; oxaliplatin, about 85 mg/m$^2$; irinotecan, about 180 mg/m$^2$; and leucovorin, from about 200 mg/m$^2$ to about 400 mg/m$^2$.

In another embodiment the present disclosure generally relates to methods of inhibiting autophagy in cancer cells by increasing the levels of miR-29 expression. Increasing the levels of miR-29 expression in the cancer cells can inhibit late stage autophagy, which has been linked to metastasis and continued growth in cancers. Similarly, higher expression levels of miR-29 can inhibit autophagosome-lysosome fusion, which is necessary for the process of autophagy to be carried out in a cell.

In another aspect, the present disclosure is directed to methods of decreasing expression of the autophagy proteins, and in particular, transcription factor—EB (TFEB) and autophagy-related protein 9A (ATG9A). These are two critical autophagy proteins that have conserved miR-29 binding sites in their 3'-UTRs. Overexpression of miR-29 has been found to reduce expression of TFEB and ATG9A. Knockdown of TFEB in PDAC reduces tumor progression and impairs autophagy through lysosome dysfunction. ATG9A is the only transmembrane protein that facilitates membrane trafficking of the autophagosomes.

Examples 1-4

Materials and Methods.
Cell Lines.
Normal human pancreatic epithelial cell lines HPNE (ATCC, CRL-4023) and HPDE (AddexBio, T0018001) were grown in Dulbecco's Modified Eagle Medium (DMEM) (Life Technologies, 11965-092) supplemented with 10% fetal bovine serum (FBS). Panc-1 (ATCC, CRL-1469) and MIA PaCa-2 (ATCC, CRL-1420) were grown in DMEM supplemented with 10% FBS, 100 units ml$^{-1}$ penicillin, and 100 mg ml$^{-1}$ streptomycin. COLO 357, AsPC-1 (ATCC, CRL-1682), and BxPC-3 (ATCC, CRL-1687) were grown in Roswell Park Memorial Institute (RPMI) 6140 (Life Technologies, 11875-093) supplemented with 10% FBS, 100 units ml$^{-1}$ penicillin, and 100 mg ml$^{-1}$ streptomycin.

RNA Purification.
Total RNA was extracted from cells using Trizol extraction kit (Life Technologies, 15596018) according to the manufacturer's protocol. The quantity and purity of RNA was determined by OD260/280 reading using a Nanodrop spectrophotometer.

Measurements of RNA by qPCR.
Mature miR-29 family member expression and p62 mRNA expression levels were measured by TaqMan Assays (Applied Biosystems): miR-29a (ID:002112); miR-29b (ID: 000413); and miR-29c (ID:000587); and SQSTM1/p62 (ID: 4331182). U6 snRNA (ID:001973) or ACTB (ID: 4331182) were used as endogenous controls to normalize miR-29 expression and p62 expression, respectively. Samples were analyzed using ABI 7500 Real-Time PCR machine. Samples were run in triplicates with 0.2 thresholds, and the $^{\Delta\Delta}$CT method was used for relative miR-29 expression analysis.

Western Blot Analyses of Proteins.
Total cell protein was isolated using RIPA buffer (Thermo Scientific, PI-89900) and quantified using BCA Protein Assay Kit (Pierce Biotechnology, 23225). Protein samples were run through SDS-PAGE and were transferred to polyvinylidene fluoride membrane, followed by a block in 10% dried non-fat milk, and then probed with primary antibodies against Caspase-3 (Novus Biological, 9662S), Procaspase-3 (Cell Signaling, 9662S), LC3B (Novus Biological, NB100-2220), SQSTM1/p62 (Thermo Scientific, H00008878-M01), LAMP-2 (Santa Cruz, sc-18822), ATG9A (ab108338), TFEB (Cell Signaling, 4240), GAPDH (Millipore, MAB374) and corresponding HRP conjugated goat anti-rabbit (Santa Cruz, sc-2004), goat anti-mouse (Bio-Rad, 172-1011), or donkey anti-goat (Santa Cruz, sc-2020) secondary antibodies. Proteins were visualized and quantified using chemiluminescent detection kit (GE Healthcare, Amersham ECL) and exposed to x-ray film (Thermo Scientific, CL-X Posure Film) or captured on an Amersham Imager 600 (GE Healthcare, CCD Model). The intensity for each band was densitometrically quantified and normalized against a loading control using ImageJ software.

Transfection of Cultured Cells.
Exponentially growing cancer cells were seeded in 6-well plates at 1×10$^5$ cells per well or 12-well plates at 5×10$^4$ cells per well and allowed to adhere overnight and transfected with indicated concentrations (10 μM, 20 μM) of control (GE Dharmacon, CN-001000-01) or miR-29a (GE Dharmacon, C-300504-07) mimics, or 1 μM siRNA using siCTRL (GE Dharmacon, D-001810-10-05), siTFEB (GE Dharmacon, L-009798-00-0005), and siATG9A (GE Dharmacon, L-014294-01-0005) using DharmaFECT®1 (GE Dharmacon, T-2001-01) as per the manufacturer's protocol. Total protein or RNA was isolated at 24 hours post-transfection for western blot or qPCR analysis respectively as described above.

Statistics.
ANOVA with Tukey's post-hoc test and 2-tailed Student's t tests were used to test for statistical significance. $P<0.05$ was considered statistically significant.

Example 1

In this Example, the effects of increased levels of miR-29 on PDAC cells' migration and invasion were analyzed. Pancreatic cancer cells were transfected with miR-29a mimics or control and plated. Cells that migrated were counted and imaged. The effects of miR-29a overexpression were also tested on anchorage dependent growth of pancreatic cancer cells using soft agar assays.

Migration and Invasion Measurements.

Figure 6A:
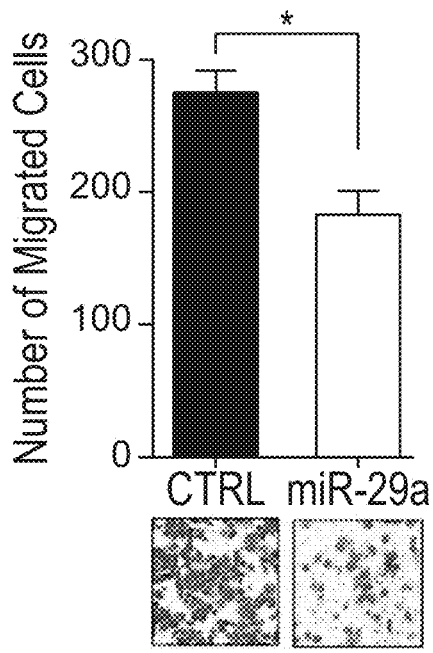
FIG. 6A-6D: Panc-1 cells were transfected with control (CTRL) or miR-29a and plated into (FIG. 6A) migration, and (FIG. 6B) invasion assays. Migration and invasion data presented as average number of cells per 5 fields (N=3) ±S.E.M. and representative images shown below each graph.
Figure 6B:
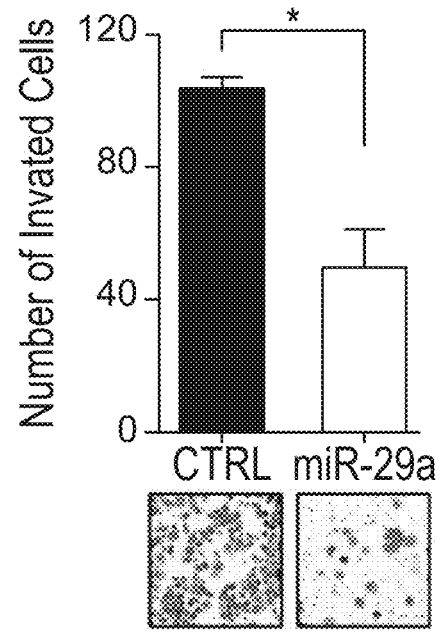
Figure 6C:
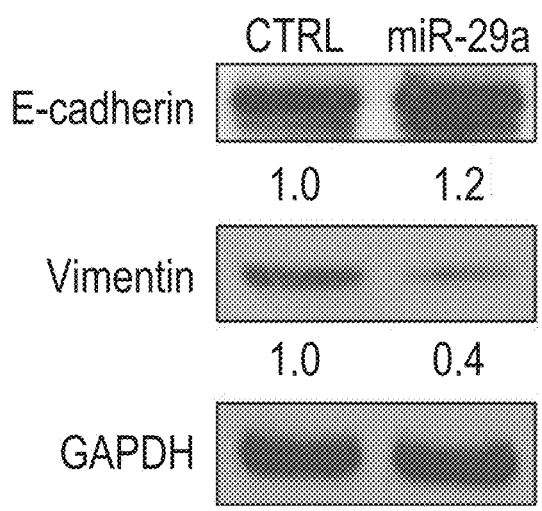

$1 \times 10^4$ cells (Panc-1 or MIA PaCa-2) transfected with 20 nM control or miR-29a mimics using DharmaFECT®1 were plated in triplicate in the upper chambers of 8 µm transwells (Falcon, 353097) in 100 µl serum-free media and 750 µl 10% serum containing media in the lower chamber of 24-well plates and incubated at 37° C. for 24 hours. For invasion assays, 80 µl of 1:5 diluted matrigel (BD, 354234) was pre-coated in the upper chambers and allowed to solidify prior to plating cells. 24 hours post-seeding, membranes were washed twice with PBS, fixed with 4% paraformaldehyde, and stained with 0.1% crystal violet in 20% ethanol. Any cells remaining in the upper chamber were carefully removed, and cells migrated/invaded on to the lower membrane were imaged and counted. For each well, 5 random fields were counted, and the average number of cells per field was presented. Compared to control cells, significantly fewer cells overexpressing miR-29a migrated through the membranes. FIG. 6A-6C.

Figure 6D:
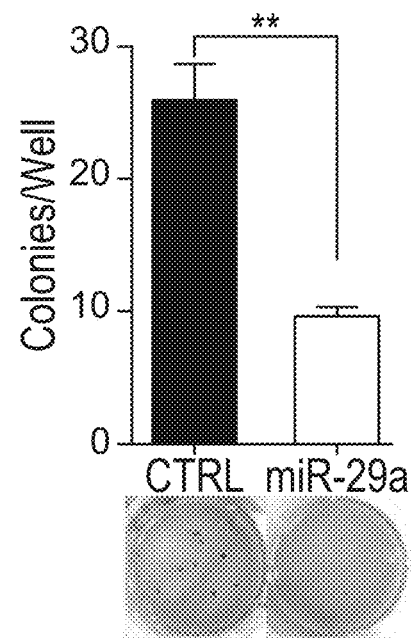
Figure 7:
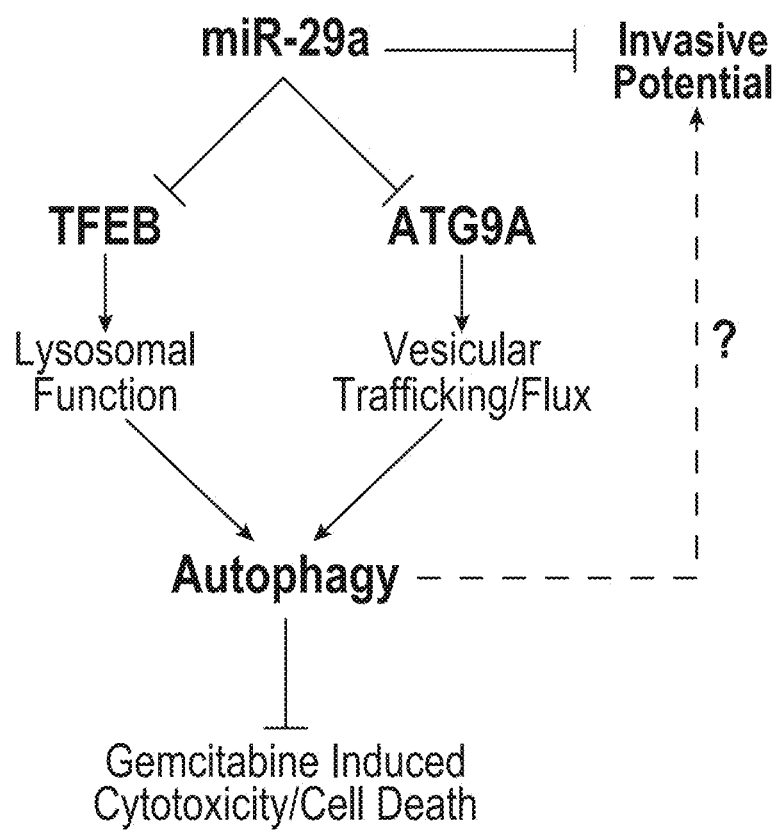
FIG. 7: schematic diagram representing the role of miR-29a in PDAC autophagy and metastasis. miR-29a overexpression in pancreatic cancer cells decreases invasive potential and inhibits autophagy flux through downregulation of TFEB and ATG9A, resulting in increased sensitivity to GEM treatment. miR-29a may serve as an anti-autophagic/invasive agent to target PDAC.

Soft agar assays. $3 \times 10^5$ pancreatic cancer cells per well (Panc-1 or MIA PaCa-2) were plated in 6-well plates and grown at 37° C. for 24 hours. Cells were then transfected with 20 nM mimic control or miR-29a mimic using DharmaFECT®. $1.5 \times 10^3$ pancreatic cancer cells (Panc-1 or MIA PaCa-2) transfected with control or miR-29a mimics per well, were platted in a 6-well plate containing 0.5% top agarose and 1% bottom agarose (BioRad, 162-0137). After 20 days, colonies were stained with crystal violet and were counted under low power bright field microscopy for positive colonies. There was a significant decrease in the number of anchorage independently growing cancer colonies overexpressing PDAC cells compared to cells expressing control mimic FIG. 6D.

Example 2

In this Example, the effect of miR-29a overexpression on viability of known gemcitabine resistant pancreatic cancer cell lines Panc-1 and MIA PaCa-2 was investigated. Cells transfected with miR-29a mimic or control were plated and treated with gemcitabine. Cell viability was measured 72 hours after treatment. Lactate dehydrogenase release was measured 24-48 hours after treatment to measure cytotoxicity.

Measurements of Cell Viability, Cytotoxicity, and Caspase Activity.

Figure 1B:
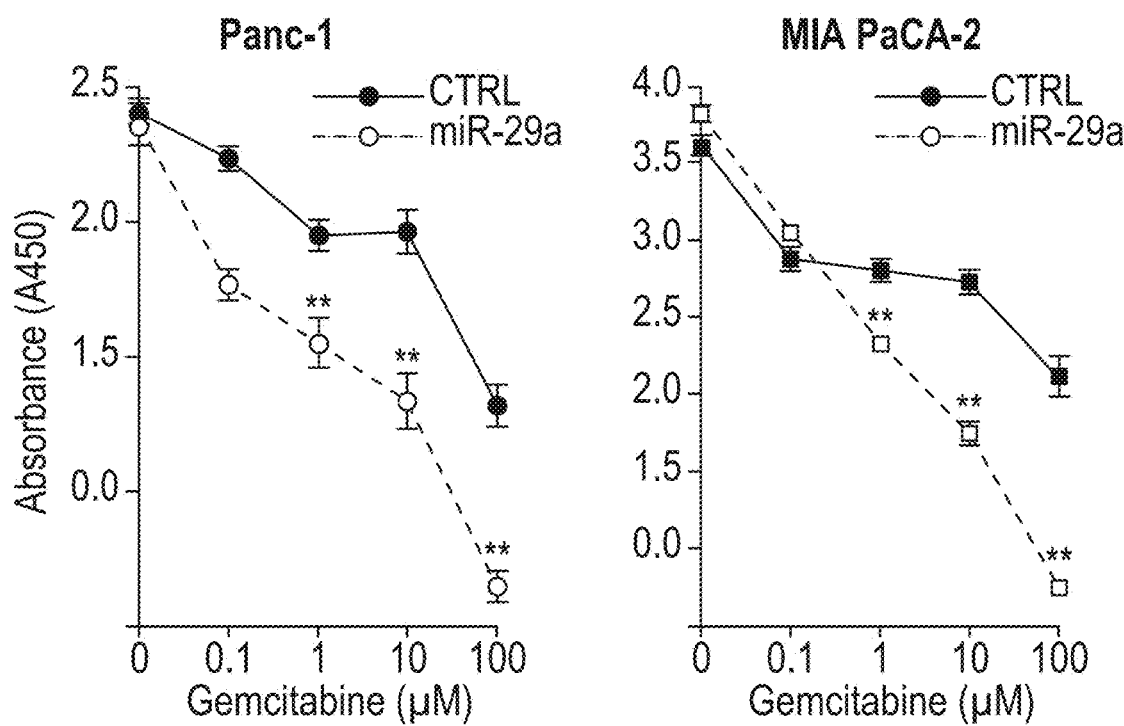

$5 \times 10^3$ pancreatic cancer cells per well (Panc-1, MIA PaCa-2, or COLO 357) were plated in 96-well plates and grown at 37° C. for 24 hours. Cells were then transfected with 20 nM mimic control or miR-29a mimic using DharmaFECT® 1 for 24 hours. Transfection media was then removed and replaced with complete media, and cells were allowed to recover for 24 hours and subsequently treated with varying concentrations of gemcitabine (0 µM, 0.1 µM, 1 µM, 10 µM, 100 µM). Cell viability was measured at 72 hours post-gemcitabine treatment by adding 10 µl Cell Counting Kit-8 (CCK8) reagent (Dojindo, CK04) and absorbance was measured at 450 nm. For cell viability with Chloroquine (CQ) and BafilomycinA1 (BafA1) treatment, cells were treated with 25 µM CQ (Sigma Aldrich, C6628) or 10 µM BafA1 (Sigma Aldrich, B1793) in combination with 10 µM gemcitabine for 48 hours, and viability was measured using CCK8 kit as described above. Overexpression of miR-29a alone did not significantly reduce the viability of cancer cells, but the addition of gemcitabine resulted in a significant decrease in cancer cell viability at various concentrations starting at 0.1 µM (FIG. 1B).

Figure 1C:
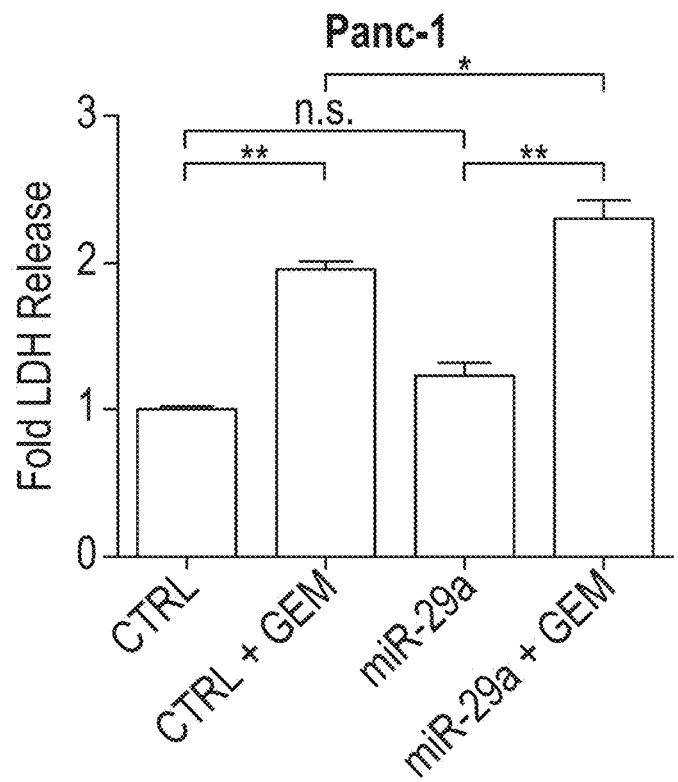
Figure 1D:
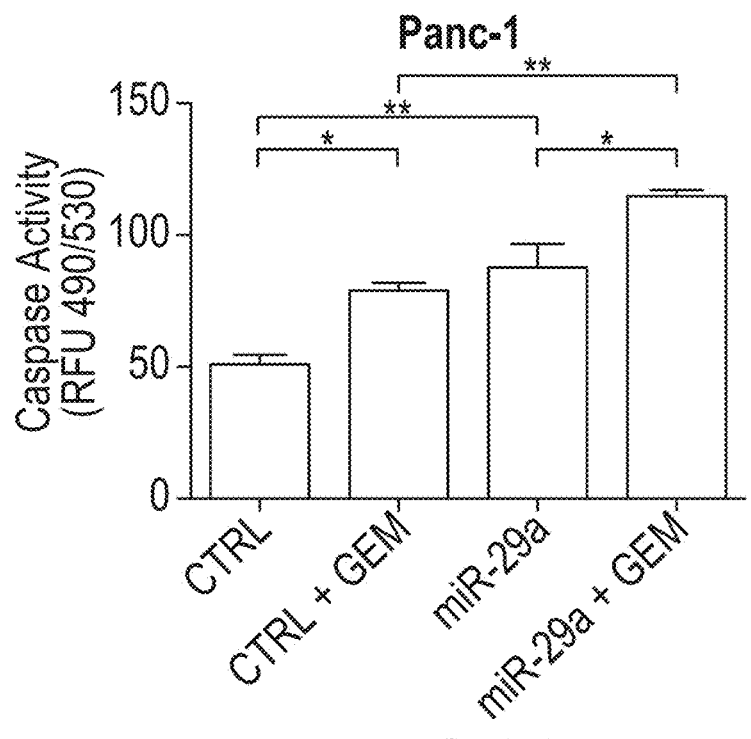
Figure 1E:
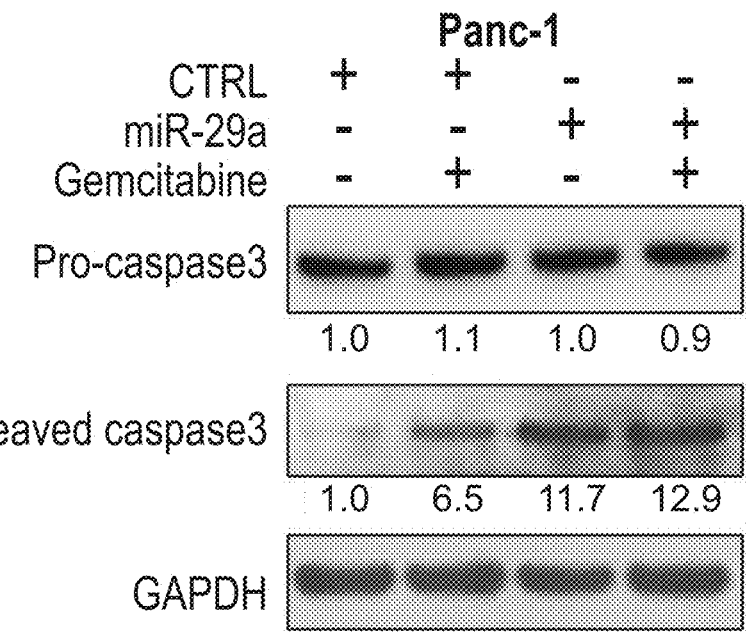

For cytotoxic effects and caspase activity, pancreatic cancer cells (Panc-1, MIA PaCa-2) were transfected with mimic control or miR-29a mimic as described above and treated with 10 µM gemcitabine for 24-48 hours. For cytotoxic effects lactate dehydrogenase release was determined using Promega CytoTox-ONE Homogeneous Membrane Integrity Assay (Promega, G7890) and fluorescence was measured at 560/590 nm. Caspase activity was determined using Promega Apo-ONE Homogenous Caspase-3/7 Assay Kit (Promega, PRG7790) with fluorescence measured at 490/530 nm. There was a significant increase in LDH from the Panc-1 and MIA PaCa-2 cells overexpressing miR-29a upon gemcitabine treatment, indicating that miR-29a increases cytotoxicity in combination with gemcitabine (FIG. 1C). Increased caspase 3/7 activity (FIG. 1D) and cleaved caspase-3 levels (FIG. 1E) was also observed.

Example 3

Figure 4B:
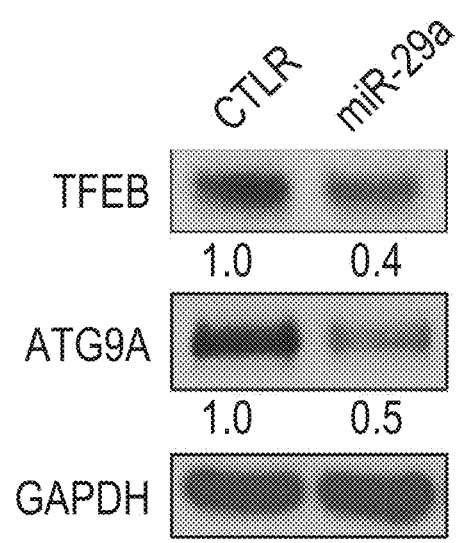
Figure 4C:
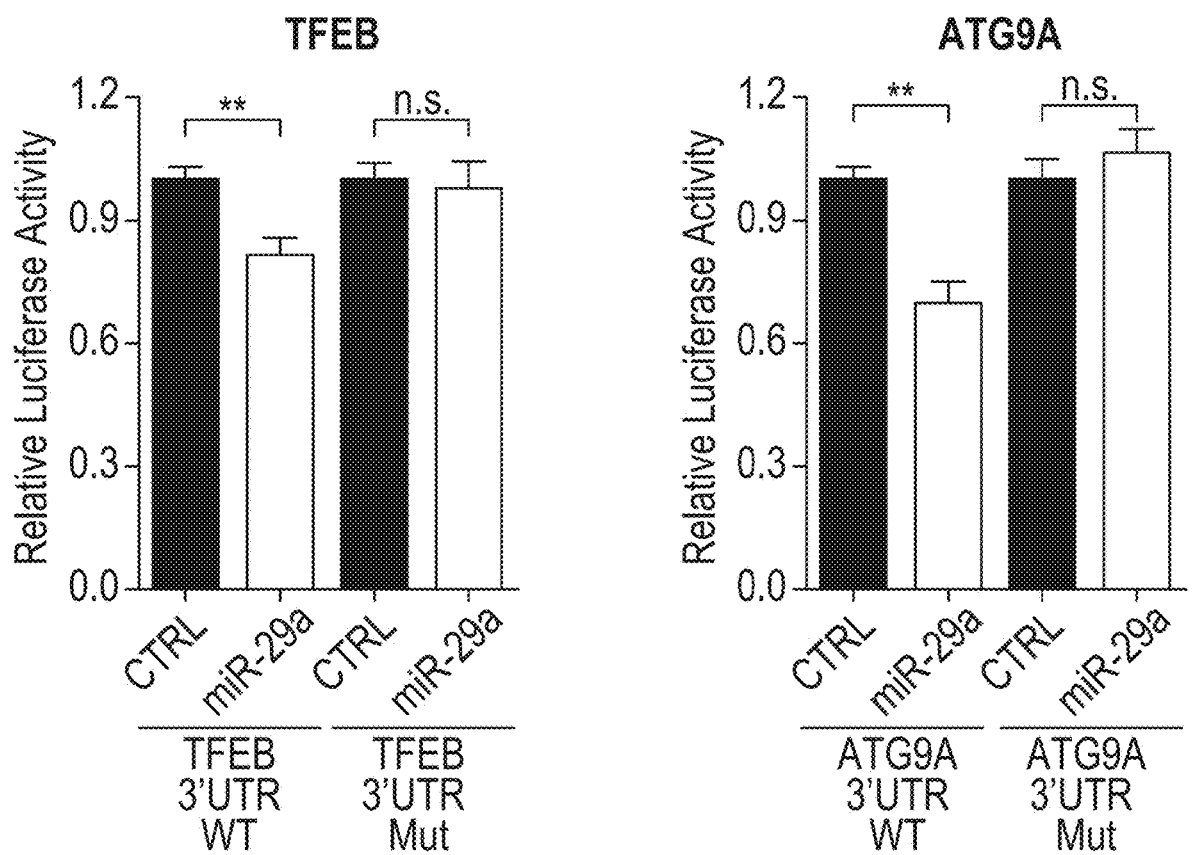
Figure 4D:
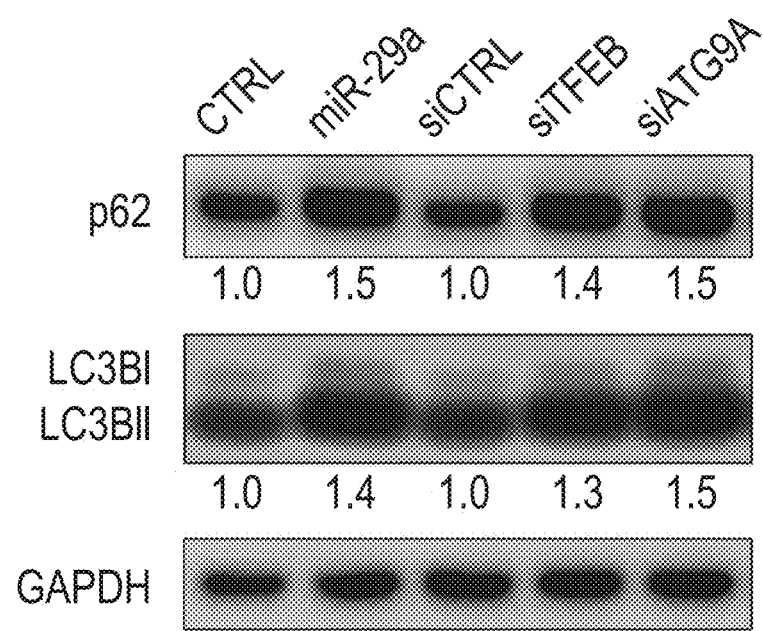

In this Example, mechanisms by which miR-29a mediates blockage of autophagy at late stages, potential autophagy related genes that are targeted by miR-29a using four prediction algorithms (TargetScan, PicTar, PITA, and miRanda) were analyzed. Transcription factor EB (TFEB) and autophagy-related protein 9A (ATG9A) were found to contain phylogenetically conserved miR-29 binding sites in their 3'-UTRs (FIG. 4A). In the western blot analysis, overexpression of miR-29a in pancreatic cancer cells resulted in a marked downregulation of both TFEB and ATG9A expression (Figure. 4B).

Luciferase Reporter Assay.

The 3'UTR containing predicted miR-29 binding sites, both wild type and mutant, for ATG9A and TFEB were cloned into pmirGLO Dual-Luciferase miRNA Target Expression Vector (Promega, # E1330) downstream of the firefly luciferase open reading frame. $5 \times 10^3$ pancreatic cancer cells per well (Panc-1 or MIA PaCa-2) were plated in 96-well plates and grown at 37° C. for 24 hours. Cells were then co-transfected 10 nM mimic control or miR-29a mimic with 100 ng of pmirGLO Dual-Luciferase miRNA Target Expression Vector containing each respective 3'UTR binding site using DharmaFECT Duo Transfection Reagent (GE, T-2010-02). Cells were transfected for 24 hours, and luciferase levels were measured 24 hours post-transfection using Dual-Glo® Luciferase Assay System (Promega, # E2920). Firefly luciferase luminescence was normalized to *renilla* luciferase activity for each transfected well.

When reporter plasmids with wild type miR-29a binding sites were co-transfected with miR-29a mimics into cancer cells, a significant repression of luciferase activity was observed. However, when the 3'UTRs were mutated, miR-29a no longer had the ability to repress luciferase activity of both TFEB and ATG9A, demonstrating that miR-29a represses TFEB and ATG9A expression by directly interacting at the predicted sites.

Figure 5A:
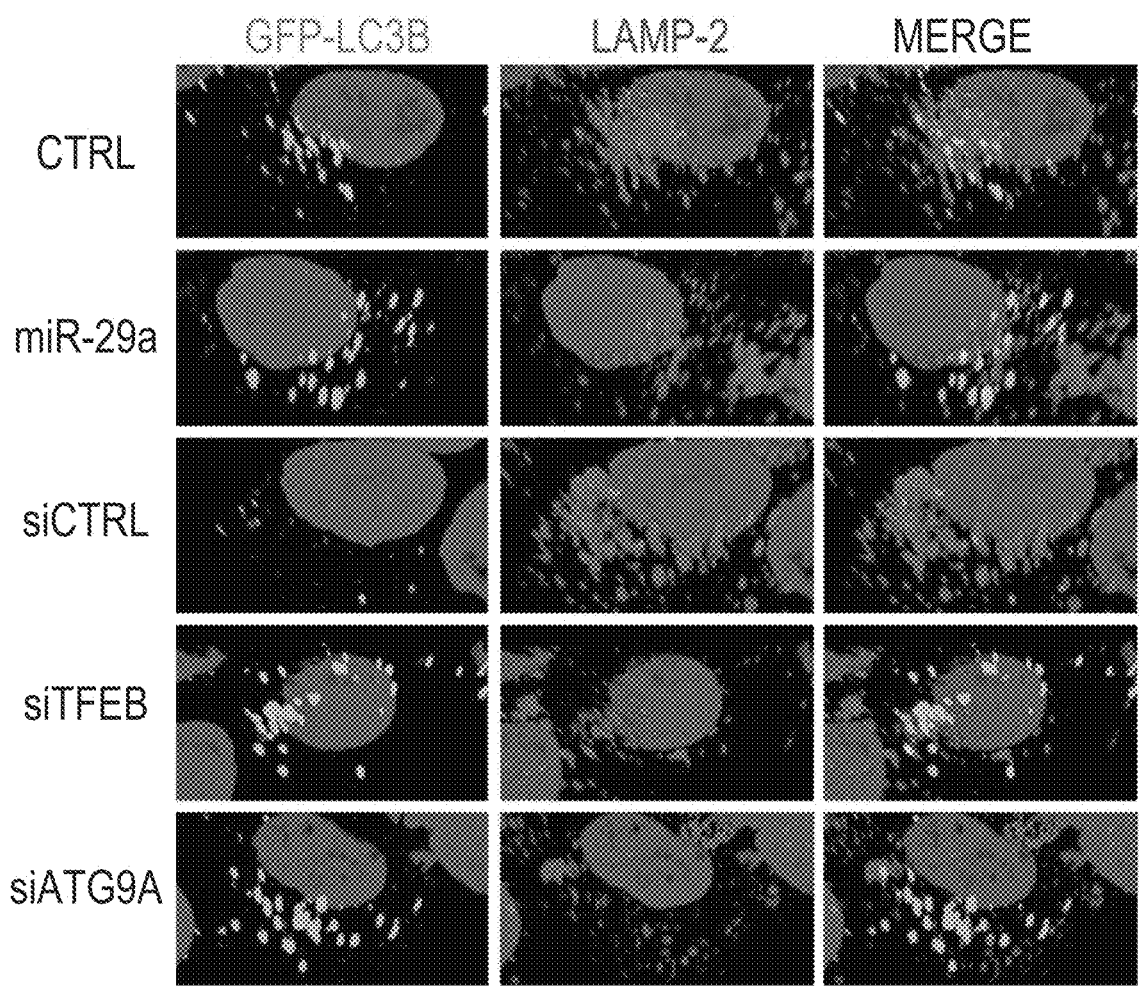
FIGS. 5A-5C.
Figure 5B:
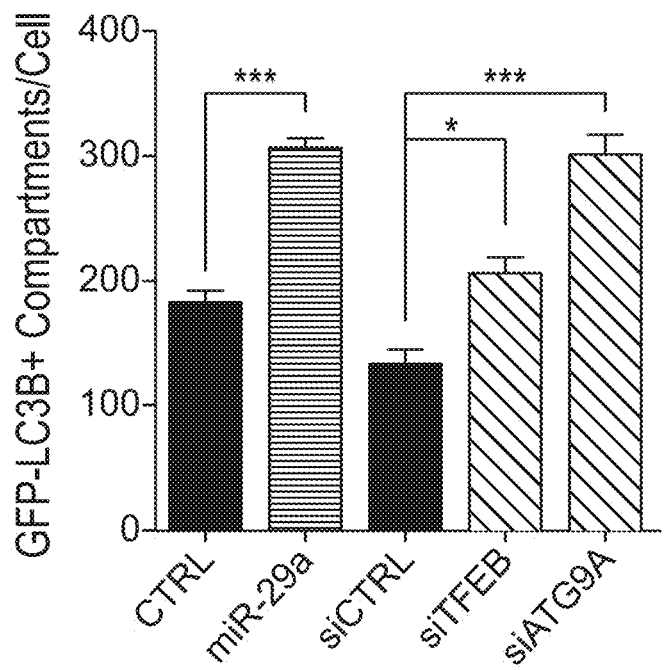
Figure 5C:
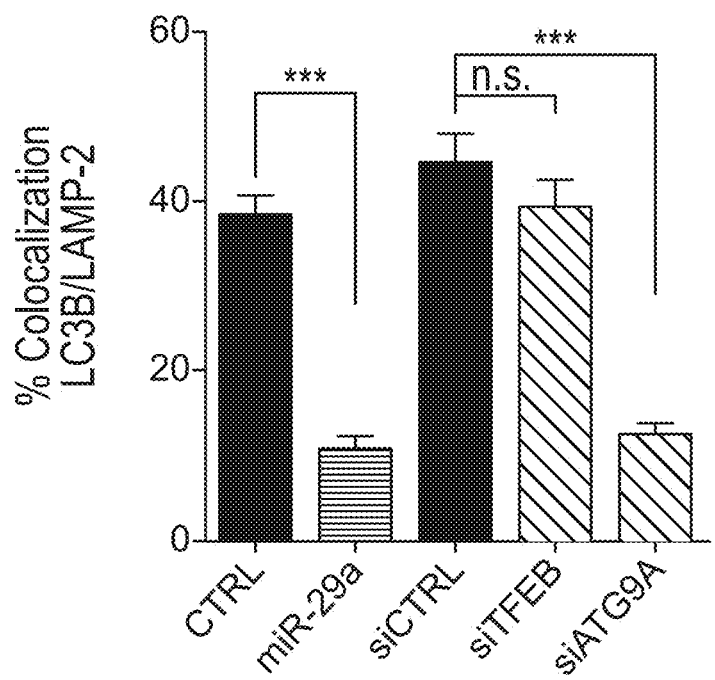

Next, the effects of TFEB and ATG9A depletion on PDAC autophagy using siRNA mediated knockdown of TFEB or ATG9A were analyzed. TFEB knockdown resulted in a ~50% increase of autophagosome accumulation, whereas ATG9A knockdown caused a >100% increase in autophagosome accumulation (FIGS. 5A and 5B). Knockdown of ATG9A resulted in a robust 2-fold decrease in colocalization of LC3B and LAMP-2, demonstrating that miR-29a inhibited autophagosome-lysosome fusion predominately by deregulation of ATG9A (FIGS. 5A and 5B).

Example 4

In this Example, the effects of miR-29 on autophagy, to determine whether the increased sensitivity and cytotoxic effects of gemcitabine in chemotherapeutic resistant pancreatic cancer cells is due to alterations in autophagy, were investigated. Panc-1 cells, which have high basal levels of autophagy, were transfected with miR-29a or mimic control and LC3B levels were assessed by western blot analysis.

Autophagy Assays.

For assessment of miR-29 effects on autophagy flux via immunoblotting, $1 \times 10^5$ pancreatic cancer cells per well (Panc-1, MIA PaCa-2, or COLO 357) were plated in 12-well plates and grown at 37° C. for 24 hours. Cells were then transfected with 10 nM control or miR-29a mimics using DharmaFECT®. 24 hours post-transfection, cells were treated with 25 µM CQ in complete media for 3-6 hours. Subsequently, total proteins were harvested and subjected to western blot analysis as described above. Lentivirus encoding GFP-LC3B were generated using plasmid (GeneCopoepia, EX-T0824-Lv103) in HEK293 cells (ATCC, CRL-1573) via standard HEPES/Calcium Phosphate transfection. Stable Panc-1 GFP-LC3B cells were generated by transducing exponentially growing Panc-1 cells in T-75 flask. GFP positive cells were selected by flow cytometry and were expanded for one week prior to conducting experiments. For immunofluorescence imaging, cells were fixed with 4% PFA and permeabilized using 0.1% triton and blocked using 1% BSA. Primary LAMP-2 antibody (Santa Cruz, SC18822) was incubated overnight, followed by secondary Alexa Fluor® 647 antibody (Abcam, ab150079) incubation and 10 µg/mL Hoechst (Life Technologies, ab150083). Eight 0.5 micron Z-stack sections were captured using the Opera (Perkin Elmer) fluorescent microscope and final images were deconvolved and analyzed using Volocity imaging analysis software (Perkin Elmer). Quantifications for number of GFP-LC3B positive compartments and colocalization of GFP-LC3B and LAMP-2 were taken from 4 random fields with 8-10 cells per field.

Figure 2A:
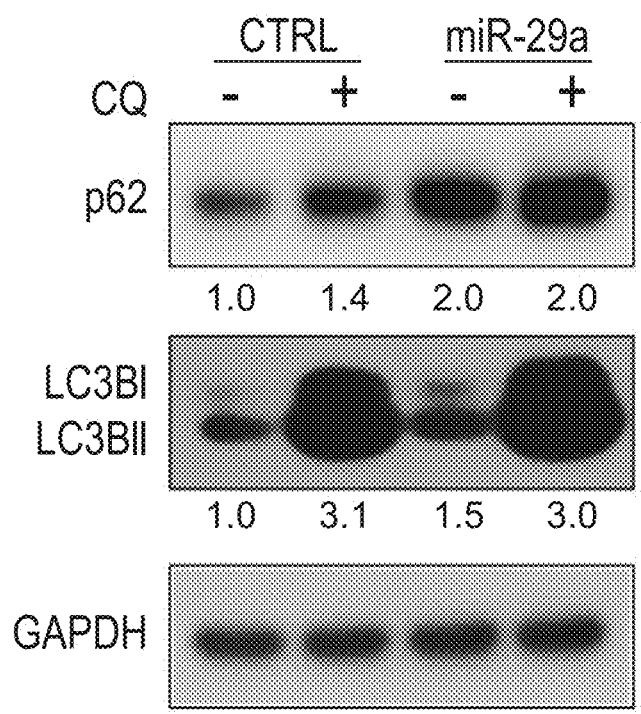
FIGS. 2A & 2B.

There was a marked increase in LC3B upon miR-29a overexpression in Panc-1 cells (FIG. 2A). An increase in p62 levels correlates with an inhibition in autophagy, whereas a decrease indicates induction of autophagy. There was a robust increase in accumulation of p62 in miR-29a overexpressing cancer cells (FIG. 2A) suggesting that miR-29a causes a late stage blockage in autophagy flux.

To further assess the effect of miR-29a on autophagy flux, miR-29a or mimic control was transiently expressed in Panc-1 cells and then treated with CQ. The results showed a robust net increase in LC3BI and II and p62 accumulation in control cells upon CQ addition. However, when miR-29a was overexpressed, prior to CQ treatment, the net difference of LC3B and p62 between miR-29a alone compared to miR-29a and CQ combination treatment was low as miR-29a had already blocked autophagy (FIG. 2A).

Figure 2B:
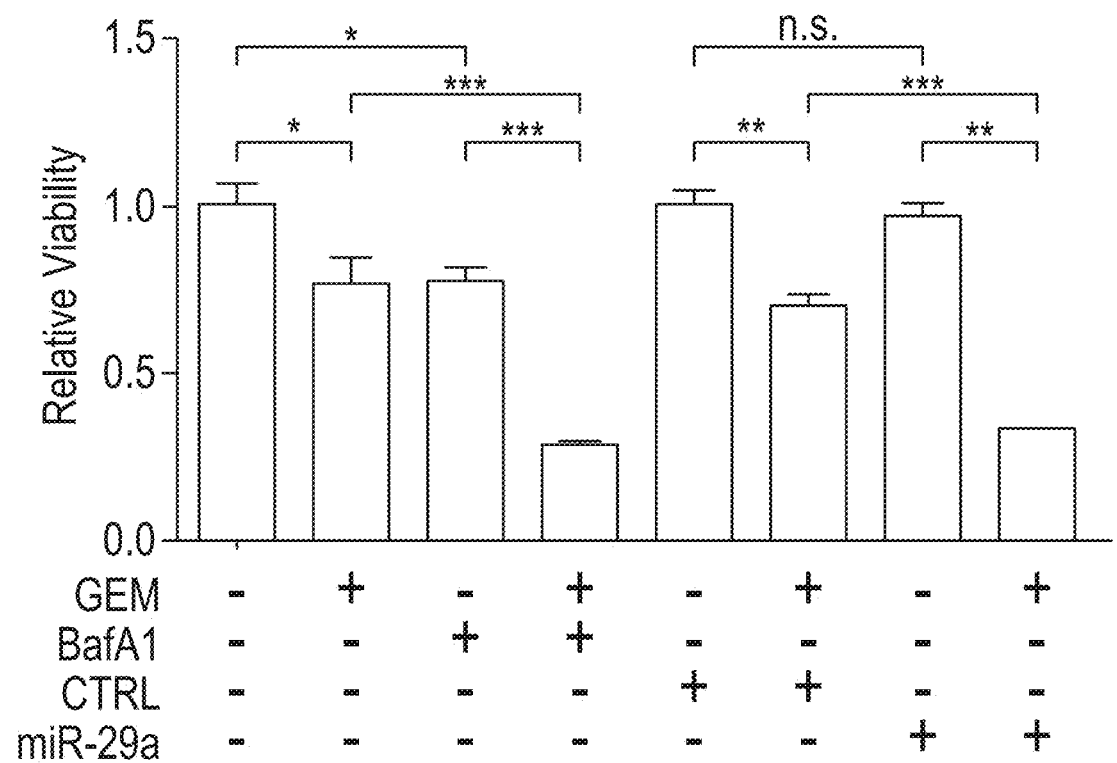

The effects of miR-29a on cancer cell viability in comparison with BafA1 were evaluated to verify the functional effect of miR-29a mediated blockage of autophagy flux on gemcitabine sensitization. Similar to miR-29, treatment of cancer cells with gemcitabine in combination with BafA1 decreased cancer cell viability (Panc-1 and MIA PaCa-2) compared to gemcitabine alone (FIG. 2B). These findings suggest that miR-29a functions as a late stage autophagy inhibitor and sensitizes chemoresistant pancreatic cancer cell lines (Panc-1 and MIA PaCa-2) to gemcitabine treatment.

Figure 3A:
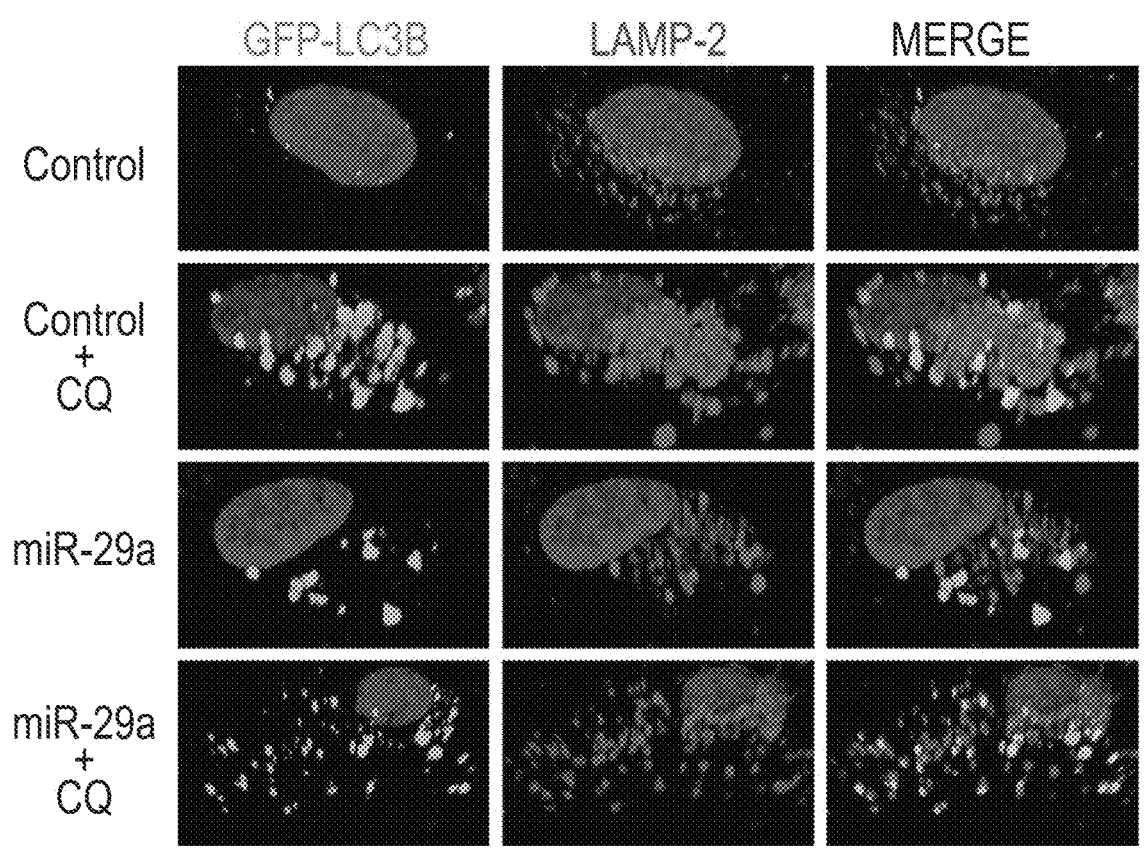
FIGS. 3A-3C.
Figure 3B:
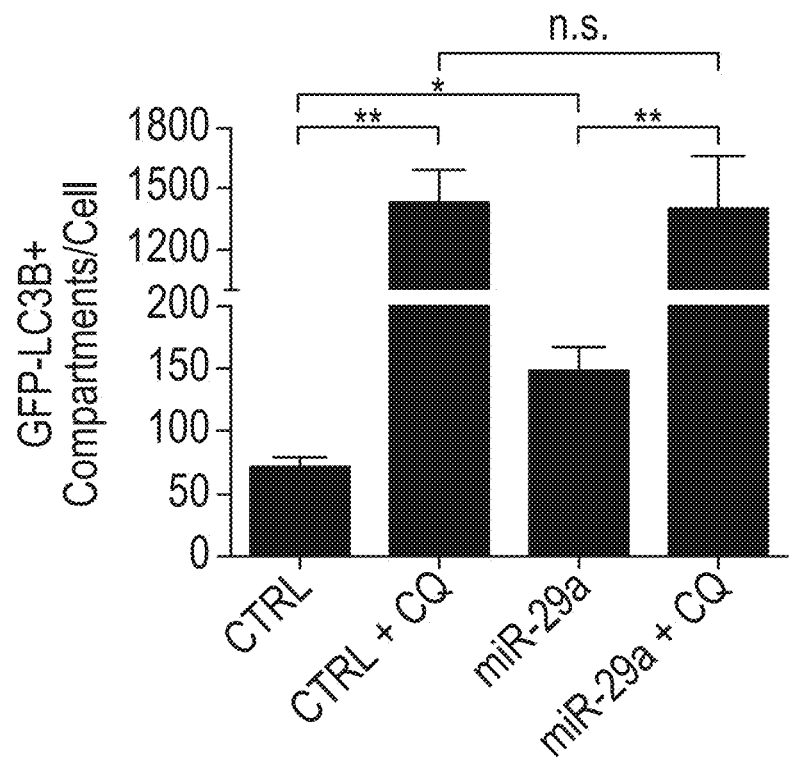
Figure 3C:
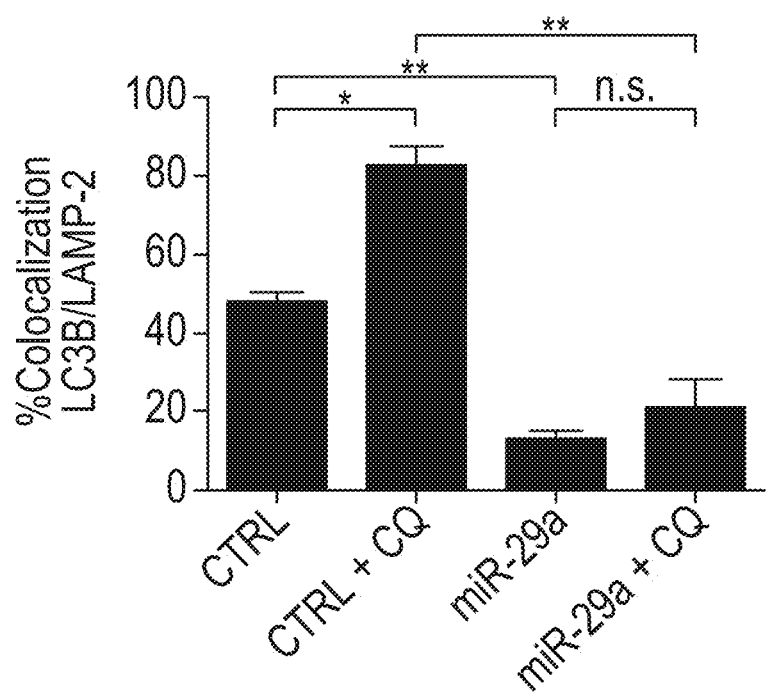

To understand the mechanisms by which miR-29a mediates blockage of autophagy flux, its impact on autophagosomes and their interactions with lysosomes were evaluated. In subsequent image analysis, a two-fold increase in accumulation of autophagosomes/autophagolysosomes in miR-29a overexpressing cells was observed (FIG. 3A). Furthermore, overexpression of miR-29a resulted in a >35% decrease in LC3B/LAMP-2 colocalization at basal levels and >60% decrease in miR-29a overexpressing cells treated with CQ, compared to CQ alone (FIGS. 3A and 3C), indicating miR-29a mediated a blockage of autophagosome-lysosome fusion.

Example 5

In this Example, the use of three scAAV serotypes-AAV6, AAV8 and AAV9- to target the pancreas via systemic delivery or retrograde ductal delivery were investigated, and the vector dose was optimized to maximize pancreatic gene expression. In addition, the effect of ductal delivery mediated pressure on pancreatitis and use of AAV to target the pancreas in a PDAC mouse model driven by KrasG12D, a common Kras mutation found in PDAC, was evaluated.

Materials and Methods.

AAV Vector Production

A self-complementary recombinant AAV vector encoding a green fluorescent protein expressing under ubiquitous EF1α promoter was produced. Particularly, recombinant AAV vectors were produced by a standard triple transfection calcium phosphate precipitation method using HEK293 cells (ATCC, CRL-1573). The production plasmids were: (i) scAAV.GFP (ii) rep2-cap6/8/9 modified AAV helper plasmid encoding the cap serotype 6, or 8 or 9, and (iii) an adenovirus type 5 helper plasmid (pAdhelper) expressing adenovirus E2A, E4 ORF6, and VA I/II RNA genes. Purification was accomplished from clarified HEK293 cell lysates by sequential iodixanol gradient purification and ion exchange column chromatography using a linear NaCl salt gradient for particle elution. Vector genome (vg) titers were determined by quantitative polymerase chain reaction (qPCR) using EF1 primer and probe set.

AAV Transduction Efficiency

Transduction efficiency was determined by counting the number of GFP+ and negative acinar or ductal cells using four random 20×GFP and DAPI overlap images. To further quantify transduction, GFP transgene qPCR was performed on total DNA isolated from pancreatic and liver tissues. Total tissue DNA was isolated using the Gentra Puregene kit (Qiagen) according to the manufacturer's instructions. 60 ng of DNA (10,000 cell equivalents) was used as PCR template in triplicate reactions and vg numbers were extrapolated from a linearized plasmid standard. Vector genome/cell calculations assumed 6 pg of total DNA per cell using GFP primer and probe set.

Histology and Microscopy

Whole Organ Pancreatic GFP Expression.

At necropsy, the abdominal cavity was opened, and the whole pancreas was imaged for GFP expression using LEICA dissecting fluorescent microscope.

H&E, Masson's Trichrome/Sirius Red Staining

After formalin fixation, specimens were dehydrated through a graded series of ethanols, cleared in two changes of xylenes and infiltrated through 3 changes of melted paraffin. The specimens are then embedded in melted paraffin and allowed to harden. Thin sections (~5 μm) were cut using a rotary microtome equipped with disposable steel knives. Sections were flattened on a heated water bath, floated onto microscope slides and dried. Serial sections were de-paraffinized and stained for Hematoxylin and Eosin and Masson's Trichrome staining (Sigma-Aldrich, HT15-1KT) and Picro-Sirius Red to detect pancreatic fibrosis following standard histological procedures or as per the manufactures instructions.

B220-Immunohistochemistry

Antigen retrieval was performed at high pH in the Dako Link PT module. After treating with a protein block (Dako) for 10 minutes the slides were incubated with CD45 (clone B220) antibody (BD Pharmingen, BD-550286, 1:50) primary antibody for 60 minutes, followed by biotinylated-anti-rat IgG (Jackson Immuno-Research) for 30 minutes, and finally with LSAB2-SA-HRP (Dako) for 30 minutes. The chromogen was developed with DAB (Dako). All steps were separated by tris buffer (Dako) washes and performed at room temperature. All histological stains were performed by histology cores at IU School of Medicine.

PanIN Analysis in KC Mice

Using a standard H&E slide, small clusters of abnormal small ducts were looked at as a first target. Using the classification system from Johns Hopkins School of Medicine (Hruban, R. H. et al. Pancreatic intraepithelial neoplasia: a new nomenclature and classification system for pancreatic duct lesions. Am J Surg Pathol 25, 579-586 (2001)), these clusters of abnormal small ducts were classified in grades 0 (normal), 1-A, 1-B, 2, and 3. Each duct in the cluster was scored.

Fibrosis and Immune Response Quantification

Trichrome: The slides were analyzed using Aperio Imagescope. The normal FDA approved algorithm for image analysis was used to detect a brown against a blue stain in immunostains. With Trichrome, the algorithm was altered to detect blue against a red background. Hue Value was altered from a 0.1 (Brown) to 0.62 (Blue). Hue width was altered from 0.5 to 0.4. Color saturation was altered from a 0.04 to 0.005. Using this algorithm, the entire tissue was analyzed, with the exclusion of vessels, pancreatic lymph nodes, and peri-pancreatic fat.

Sirius Red: Using Aperio Imagescope, the slides were analyzed using an altered algorithm. The altered algorithm was modified from the FDA approved algorithm for immunostains. Hue value was altered from a 0.1 (Brown) to 0.85 (Red). Hue width was not altered. Color saturation was altered from a 0.04 to 0.6. The intensity threshold from moderate to low was lowered from 175 to 100. The entire pancreatic tissue was analyzed, with the exclusion of large vessels, pancreatic lymph nodes, and peri-pancreatic fat.

B220: A pathologist reviewed the slides to determine an estimate of the quantity of cells that were stained B220 positive.

CK19 and SMA

Frozen sections (7 μm) were rehydrated in PBS, permeabilized with 0.5% Triton X solution, blocked with 10% BSA, and probed with either alpha SMA antibody (Novus Biologic, NB500-631, 1:200) or CK19 antibody (Abcam, ab52625, 1:200) overnight at 4° C. For CK19 staining, epitope retrieval was performed using 1× sodium citrate buffer followed by Triton X permeabilization. Subsequently, slides were stained with secondary antibody Alexa Fluor 594 goat anti-rabbit IgG (Life Technologies, A11037, 1:1000). Slides were mounted with Vectashield antifade mounting medium with DAPI (Vector Laboratories, H-1200) and coverslips were sealed.

Retrograde Pancreatic Ductal Delivery

Mice were sedated using isoflurane with 1.5-3% oxygen, the abdominal cavity was opened, and a customized catheter was inserted into the cystic duct through a small opening at the bottom of the gallbladder. The catheter was then advanced into the common bile duct and secured in place with a micro clamp around the bile duct and catheter to prevent vector reflux into the liver. A micro clamp was placed on the sphincter of Oddi to avoid leakage of the vector into the duodenum, and 100 μl of AAV vector containing the GFP transgene or PBS (vehicle control) was slowly injected into the pancreatic duct through the catheter. Successful administration was documented by uniform swelling of the gland. The micro clamps used to temporarily block liver infusion and duodenum leak were released 5 minutes after the infusion was completed. The catheter was then removed, the inner abdominal cavity was closed with absorbable sutures, and the outer skin was closed with wound clips. Post-surgery, mice were placed on a heating pad to maintain body temperature during recovery. Once the animals recovered, they were returned to their cages. Mice were treated subcutaneously with Carprofen (5-10 mg/kg) to prevent post-operative discomfort.

Mice. KrasG12D; Pdx1-Cre (KC) mice were generated. Conditional LSL-KrasG12D mice were crossed with Pdx1-Cre animals to generate the KC mice. All animal housing, use, and surgical procedures were carried out in accordance with the regulatory guidelines set by Guide for the Care and Use of Laboratory Animals of the National Institutes of Health. All animal protocols were reviewed and approved by the Indiana University (IU) and The Research Institute at Nationwide Children's Hospital Animal Care and Use Committee.

Statistical analysis. Student's t-test and Analysis of Variance with Tukey post-hoc analysis was used for statistical analysis. Data is presented as mean and error bars are represented as standard error of the mean.

Results.

Comparison of scAAV8 and scAAV9 Serotypes to Target the Pancreas Via Systemic Delivery.

Figure 8A:
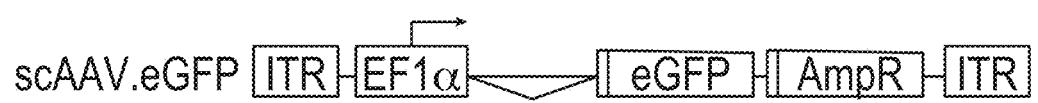
FIGS. 8A-8D: comparison of scAAV8 and AAV9 to target the pancreas via systemic delivery as analyzed in Example 5.
Figure 8B:
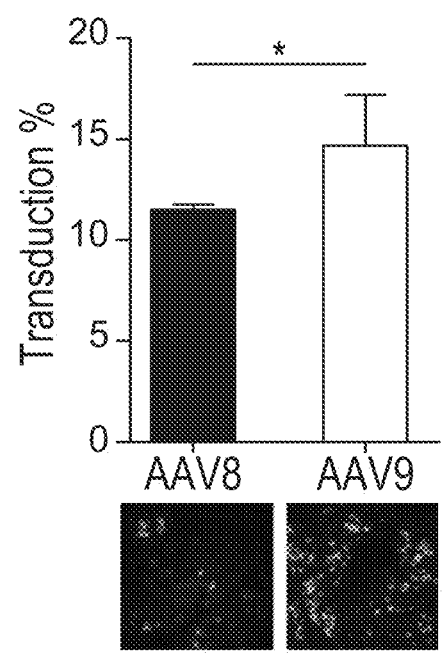

In both clinical and pre-clinical settings, either direct injection or systemic delivery to the target tissue are preferred routes of administration for therapeutic purposes because of their ease of use. As direct injection of the pancreas would be more invasive and may not achieve uniform gene expression in the entire pancreas, for this Example, systemic delivery was used. Previously, systemic delivery of ssAAV serotype 8 and 9 (AAV8 and AAV9) has been demonstrated to modestly transduce the pancreas. scAAV vectors are known to transduce target tissues with higher efficiency compared to ssAAV vectors. To test for the ideal serotype for systemic delivery, scAAV viral vector expressing green fluorescent protein (GFP) under EF1α promoter (scAAV.GFP) (FIG. 8A) was packaged using AAV8 and AAV9 serotypes, and $1 \times 10^{12}$ vg/animal were delivered systemically (n=3 mice/group) to normal C57BL/6 mice, and animals were sacrificed at 3 weeks post-vector administration. As documented by fluorescence microscopy for GFP expression, AAV9 showed modestly higher transduction efficiency (14.6%±2.5 Standard Error of the Mean—S.E.M.) compared to AAV8 (11.5%±0.2 S.E.M.) (FIG. 8B).

Figure 8C:
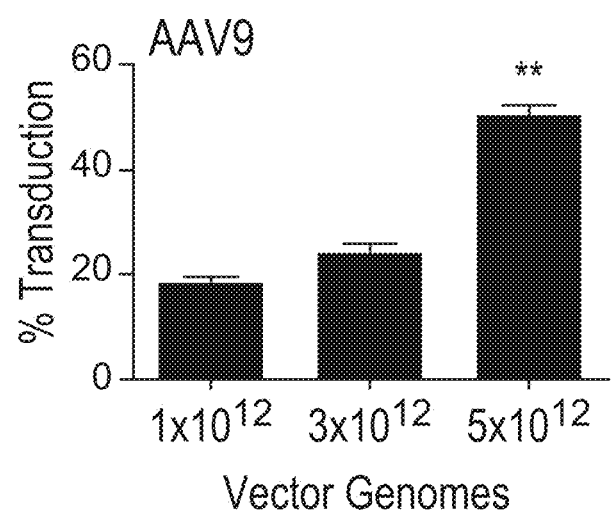
Figure 8D:
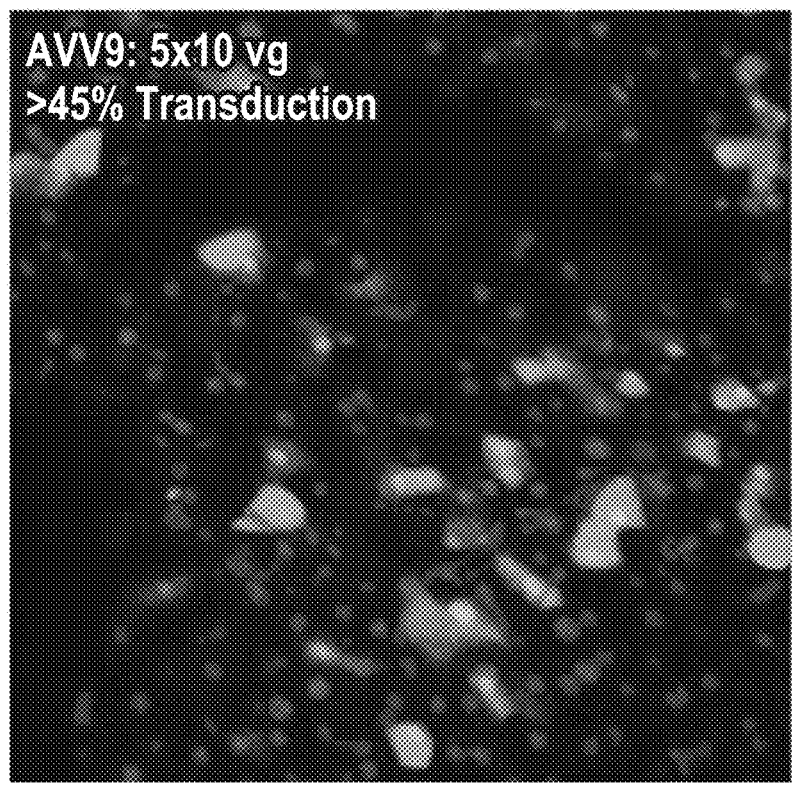

To test the ideal dose for achieving maximum pancreatic transduction efficiency via systemic delivery of scAAV9.GFP vector, three different doses ranging from $1 \times 10^{12}$-$5 \times 10^{12}$ vg/animal were compared. Although increase in vector dose improved transduction percentages, none of the tested doses reached >60% pancreatic transduction efficiency (FIGS. 8C & 8D). This level of gene expression may be sufficient to develop therapeutic strategies for non-neoplastic tissues, but in the context of cancer, optimal transduction efficiency (>90%) is preferred for therapeutic benefit and functional studies. Further, dose increase via systemic delivery may improve transduction efficiency, but clinically producing the required amounts of virus for dosing adult PDAC patients without toxicity may be challenging.

Retrograde Intraductal Infusion of scAAV6 Transduced the Pancreas Uniformly and Efficiently.

A wide range of gene delivery methods were previously evaluated to directly target the pancreas such as retrograde pancreatic ductal delivery by direct injection of the distal common bile duct, cannulation of the common bile duct through the gallbladder/cystic duct, and intravenous injection coupled with liver blockage. Although each of these methods were shown to be effective to transduce various cell types of the pancreas (acini, islet of Langerhans, and ductal cells), retrograde ductal delivery via cannulation of the common bile duct was used because this route has been shown to efficiently transduce the acinar and ductal cells, primary cells of origin for PDAC using AAV viral vectors. However, its safety profile, use in cancer settings, and long-term gene expression has not been evaluated.

Figure 9A:
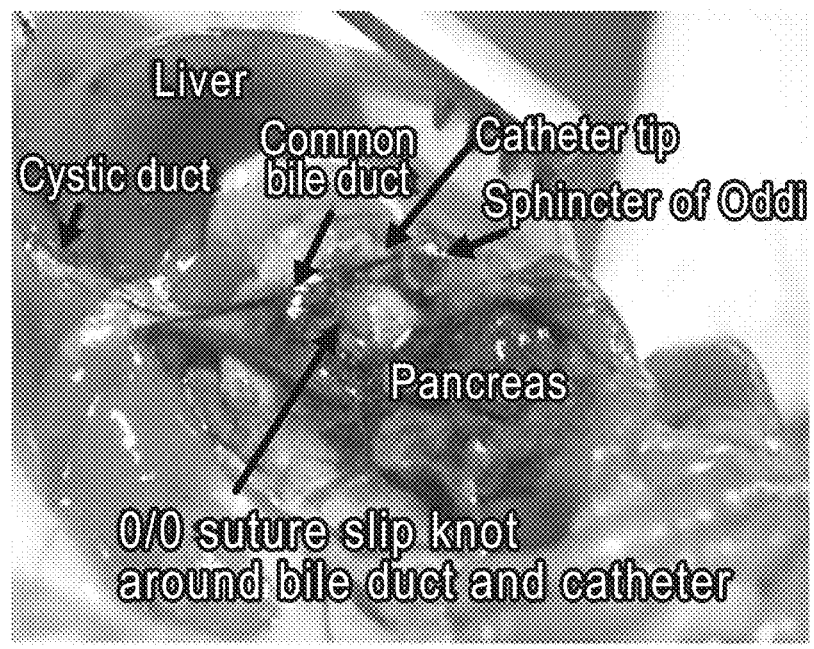
FIGS. 9A-9E: optimization of retrograde intraductal infusion via catheterizing the common bile duct through gall bladder and cystic duct.

Initially to optimize the conditions for cannulation and retrograde ductal delivery, a cohort of mice were dosed with Evans Blue dye. As elaborated in the methods section, a customized 10 mm catheter was advanced through the gallbladder and cystic duct to the common bile duct (FIG. 9A). A micro clamp is placed on the bile duct and sphincter of Oddi to prevent vector leakage into the liver and small intestine, and 100 μl of Evans Blue was injected over 2-3 minutes to target the pancreas. A uniform distribution of Evans Blue was observed in the entire pancreas (FIG. 9A).

Figure 9B:
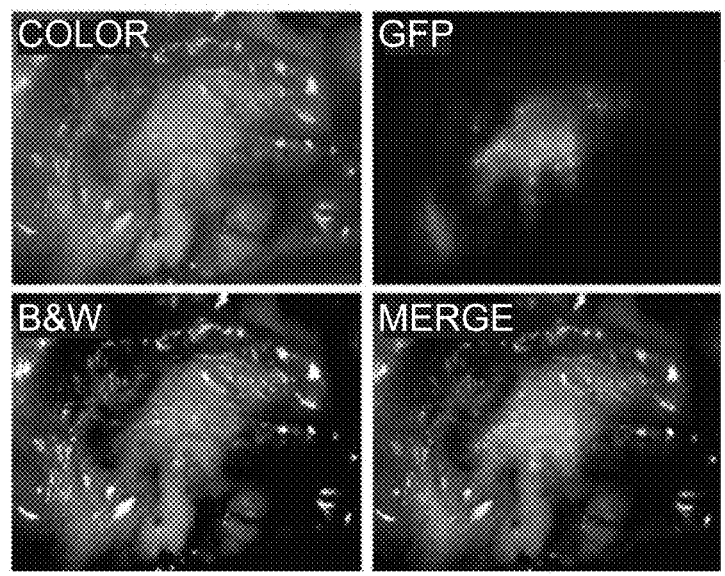

Subsequently, to test the efficacy of rAAV to target the pancreas, in this Example, scAAV.GFP was packaged with the AAV6 serotype, which has been shown to efficiently target the pancreas. We administered 1011 vg/animal of scAAV6.GFP via retrograde ductal delivery and animals were sacrificed 3 weeks later for global GFP expression analysis. As documented under direct fluorescence, scAAV6 transduced the pancreas with uniform GFP expression (FIG. 9B).

Identification of an AAV Serotype to Efficiently Target the Pancreas Via Retrograde Intraductal Infusion.

Figure 9C:
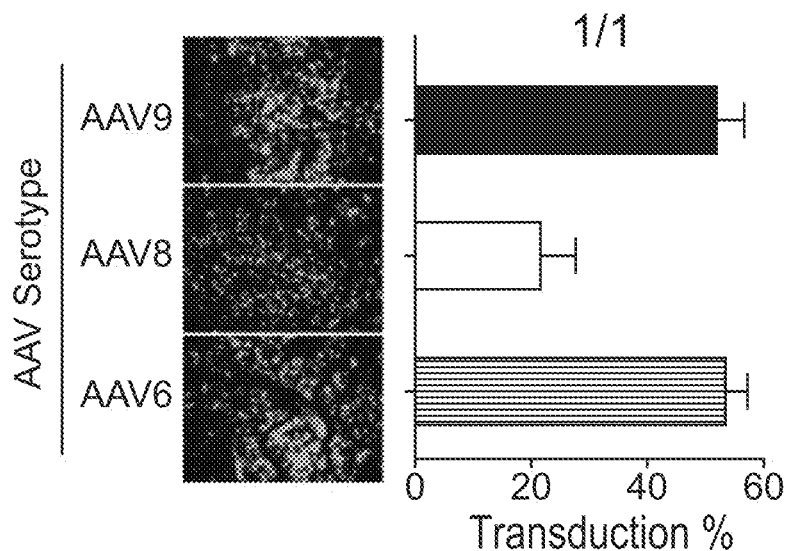
Figure 9D:
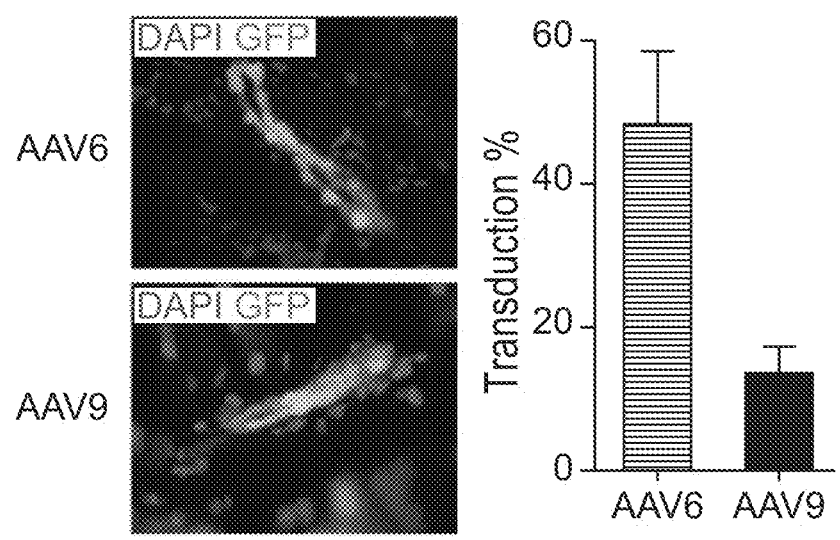
Figure 9E:
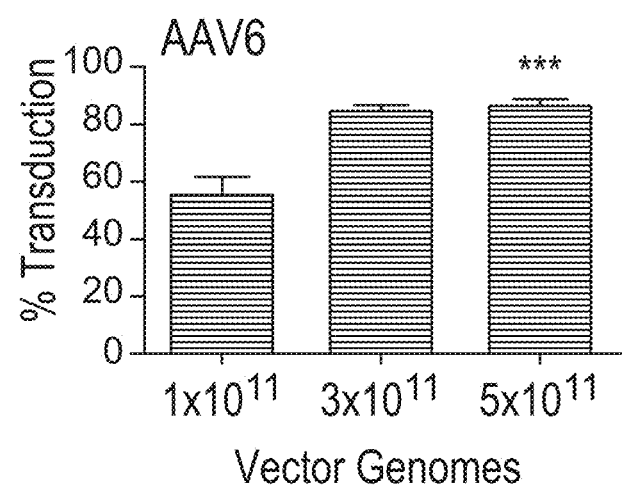

Single-stranded AAV 6, 8, and 9 serotype vectors have been shown to transduce the pancreas efficiently via retrograde pancreatic intraductal delivery. However, the efficiency of scAAV vectors has not yet been determined. To address this question, scAAV.GFP serotypes 6, 8, and 9 were compared, and a cohort of C57BL/6 mice for each serotype (n=3-4 mice/group) was dosed with 1011 vg/animal via retrograde pancreatic ductal delivery. At 3 weeks post-vector infusion, animals were sacrificed, and pancreata were collected from each animal to compare GFP transduction efficiency. As documented by fluorescent microscopy, scAAV6 and scAAV9 transduced acinar cells (exocrine cells) more efficiently with 53%±3.8 S.E.M. and 52%±2.7 S.E.M., respectively (FIG. 9C) compared to scAAV8 (21.7%±5.9 S.E.M.). Similarly, scAAV6 transduced ductal cells (48.2%±10.25 S.E.M.) GFP more efficiently compared to scAAV9 (13.6%±3.7 S.E.M.) (FIG. 9D). To achieve maximum pancreatic transduction via intraductal delivery, a cohort of mice was dosed with three escalating doses ($1 \times 10^{11}$, $3 \times 10^{11}$, and $5 \times 10^{11}$ vg/animal) using scAAV6.GFP. Quantification of the transduced exocrine acinar cells showed a proportionate increase in transduction percentages and achieved maximum gene expression at the highest dose ($5 \times 10^{11}$ vg) used (FIG. 9E).

Figure 10A:
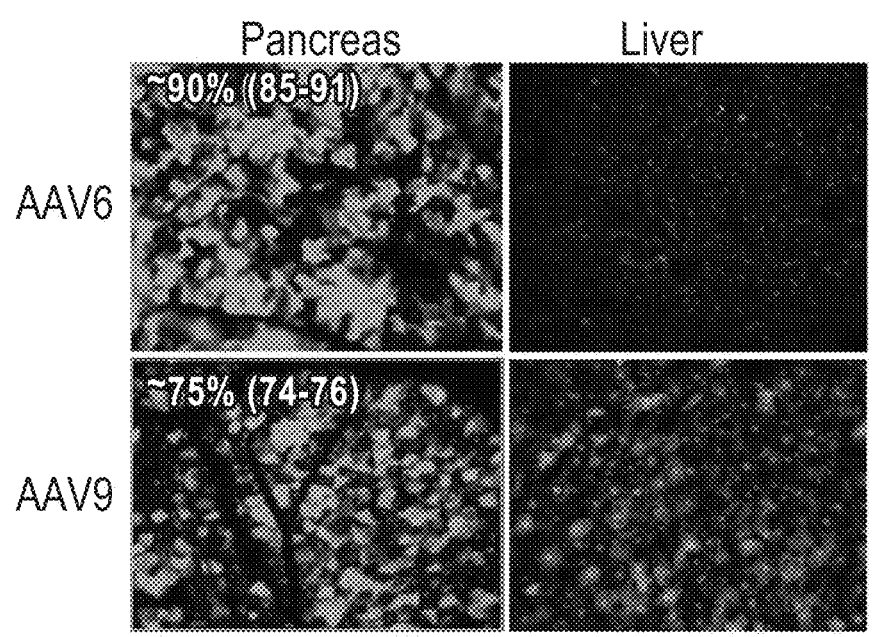
FIGS. 10A-10D: scAAV6 has increased specificity in transducing the pancreas compared to scAAV9. C57BL/6 mice were dosed with scAAV6.GFP or scAAV9.GFP at 5×10¹¹ vg/animal.
Figure 10B:
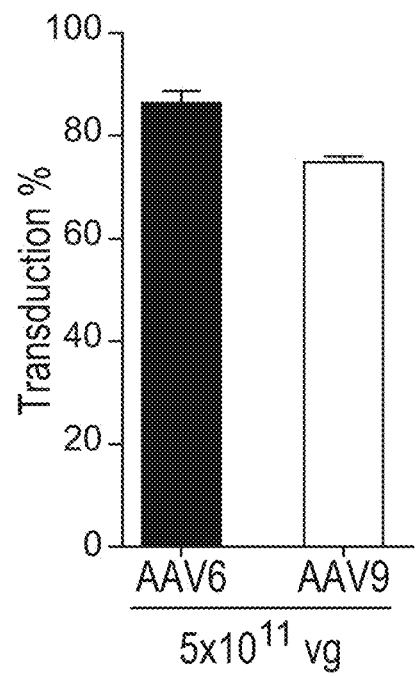
Figure 10C:
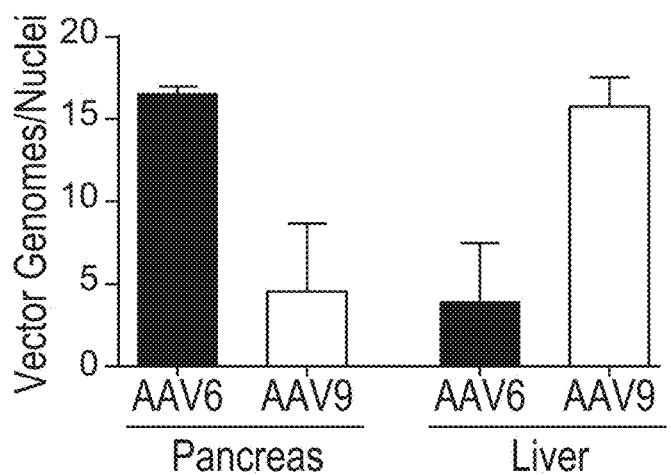
Figure 10D:
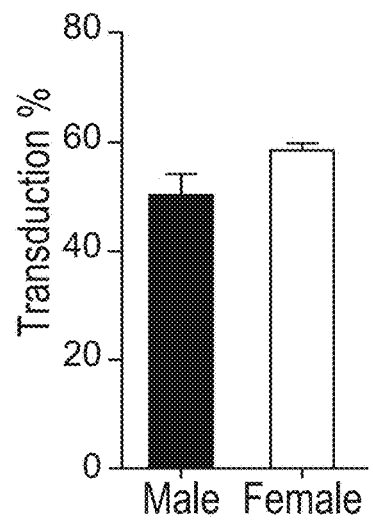

As scAAV6 and scAAV9 showed comparable transduction efficiency at the lowest dose ($10^{11}$ vg/animal), to determine maximum pancreatic gene expression in this model, the transduction efficiency of AAV6 and AAV9 was compared at a dose of $5 \times 10^{11}$ vg/animal. AAV6 had statistically significant higher pancreatic GFP expression (86%±2.4 S.E.M.) compared to AAV9 (75%±1 S.E.M.) (FIGS. 10A & 10B). GFP expression in the livers of these mice (a common off-target of intraductally dosed mice) was also examined, and AAV9 had relatively higher liver transduction percentages compared to AAV6 (FIGS. 10A & 10B). To further confirm this observation, transduced vector genomes of the pancreas and liver were quantified by quantitative real-time PCR (qPCR). AAV6 had more specificity in targeting the pancreas with more vector genomes compared to AAV9, whereas AAV9 had relatively very high vector genome copies in the liver compared to AAV6 (FIG. 10C). This phenomenon was further tested in animals dosed with $5 \times 10^{11}$ vg/animal of AAV6 and AAV9 and AAV6 was found to have more specificity in transducing the pancreas compared to AAV9. scAAV-mediated GFP expression was not found in any other tissues in the body including kidney, lung, skeletal muscle, and spleen (data not shown). Finally, to test the effect of murine gender on AAV6 mediated pancreatic transduction, a cohort of C57BL/6 males and females were dosed with $10^{11}$ vg of scAAV6.GFP (n=3 mice/group) and it was found that sex did not have a significant effect on pancreatic transduction (FIG. 10D).

AAV6 Efficiently Targeted and Showed Long-Term Gene Expression in Epithelial and Stromal Cells in PDAC Mice.

Figure 11A:
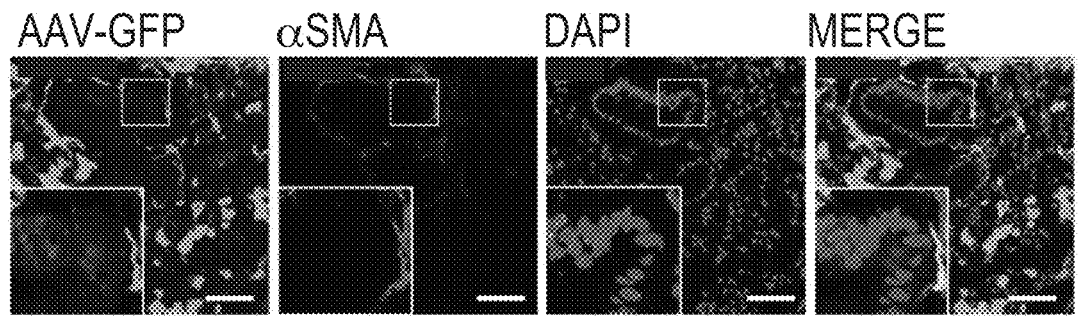
FIGS. 11A & 11B: retrograde pancreatic intraductal delivery of scAAV6 efficiently targets stromal and epithelial cell and shows long-term gene expression in PDAC mice. 5×10¹¹ vg of scAAV6.GFP was dosed in KC mice and pancreata was collected at (FIG. 11A) 3 week post-vector administration for early time point (60× inset) and (FIG. 11B) 5 months post-delivery for late time point and stained for αSMA or CK19. GFP (green), αSMA or CK19 (red), and DAPI (blue). Representative images presented. Scale bar 40 pm, 20× magnification, inset arrows indicate αSMA+/GFP+ PSCs.
Figure 11B:
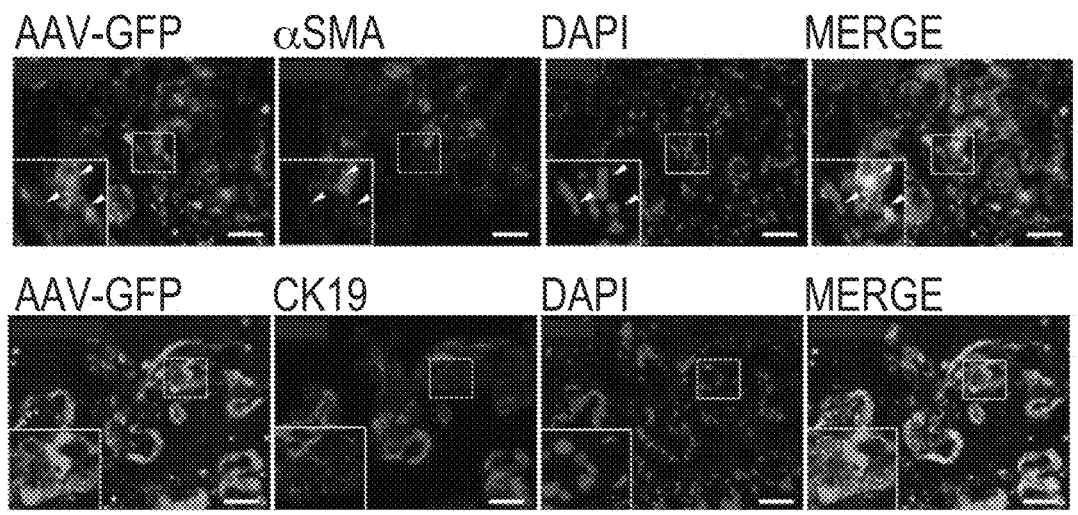

To test the feasibility of using scAAV6 to target the pancreas of PDAC mice, a cohort of a well-characterized PDAC mouse model, KrasG12D; Pdx1-Cre (KC) was dosed with scAAV6.GFP at 1 month of age via intraductal delivery. As documented via fluorescence microscopy, scAAV6 transduced KC mice pancreata very efficiently at 3 weeks post-vector administration (FIG. 11A). Although with relatively low efficiency compared to acinar cells, scAAV6 transduced pancreatic intraepithelial neoplasm (PanIN) (FIG. 11A, 60× insert). Furthermore, by staining KC mice pancreata with a pancreatic stellate cell (PSCs) specific marker, alpha smooth muscle actin (αSMA), it was found that scAAV6 transduces PSCs efficiently (FIG. 11A). PSCs are the primary cells responsible for stromal accumulation associated with PDAC tumors. Finally, to test AAV mediated long-term gene expression, the pancreata of scAAV6.GFP dosed KC mice was collected at 5 months post-injection and persistent GFP expression was found (FIG. 11B) in both PSCs (αSMA+) and epithelial/cancer cells (CK19+), demonstrating the potential use of scAAV6 to deliver therapeutic molecules/genes to pancreatic neoplasm in a stable and prolonged manner.

Retrograde Intraductal Delivery is Safe with No Evidence of Pancreatitis in Normal Pancreata Nor Enhanced Disease Progression in PDAC Mice.

Figure 12A:
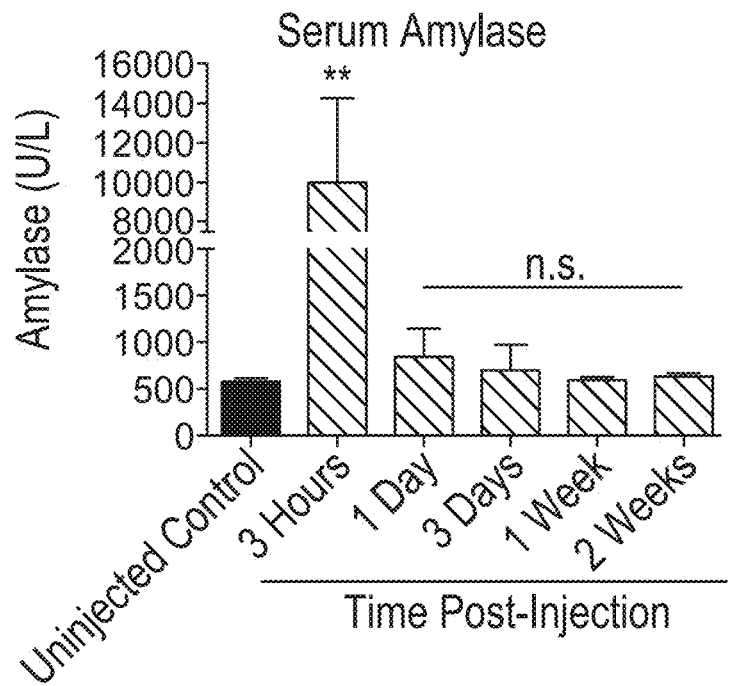
FIGS. 12A-12E: Retrograde pancreatic intraductal delivery is safe and does not induce chronic pancreatitis. Serum samples collected from intraductally dosed (100 pl PBS) C57BL/6 mice were analyzed for (FIG. 12A) amylase and (FIG. 12B) lipase. Data represents mean±S.E.M. *p<0.05, **p<0.01. n.s: non-significant.
Figure 12B:
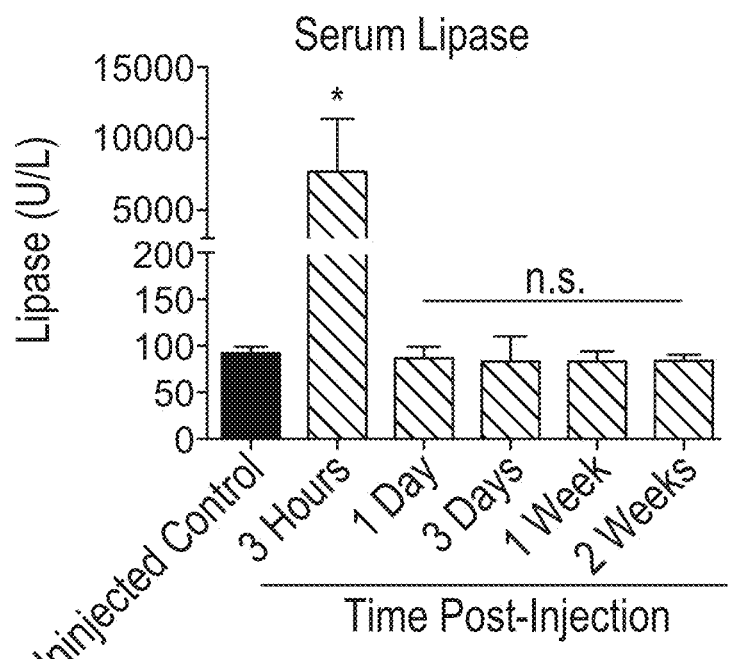
Figure 12C:
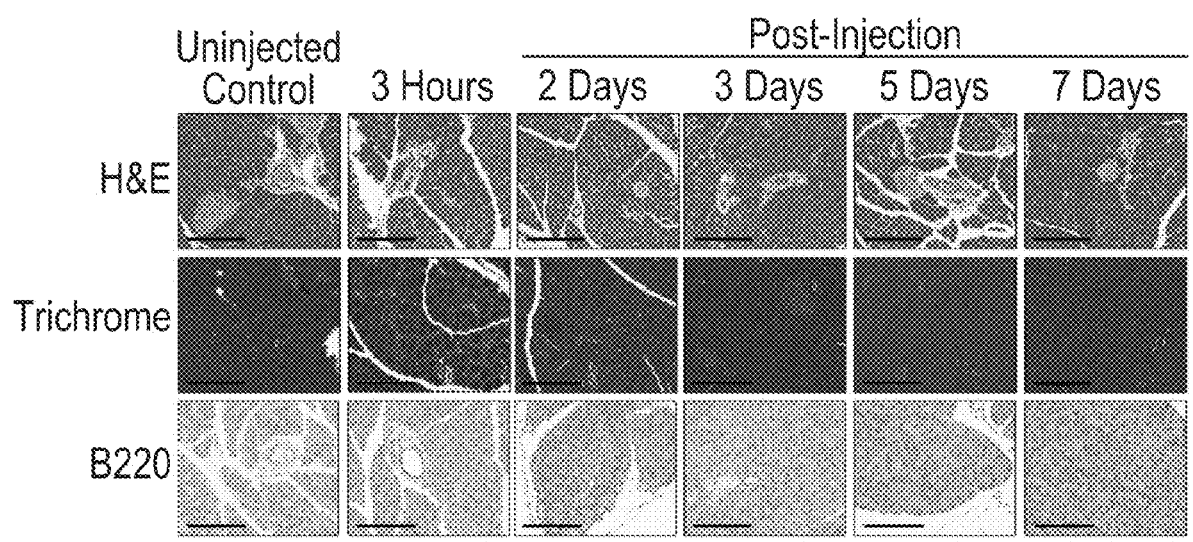
Figure 12D:
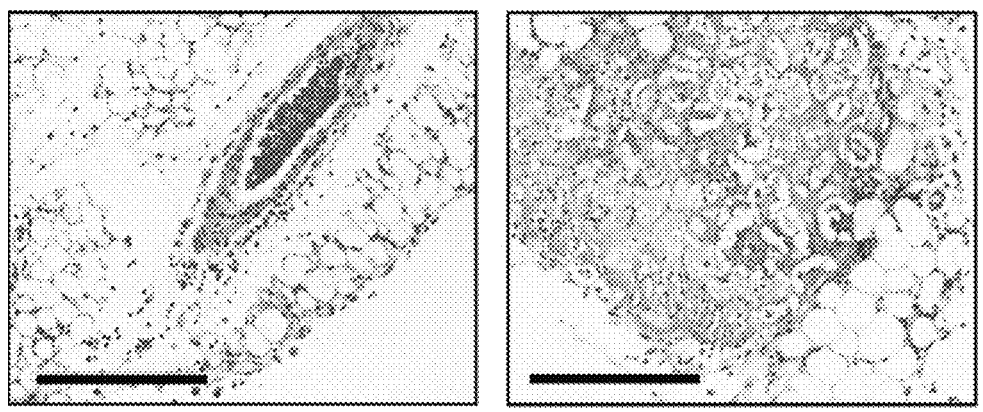
Figure 12E:
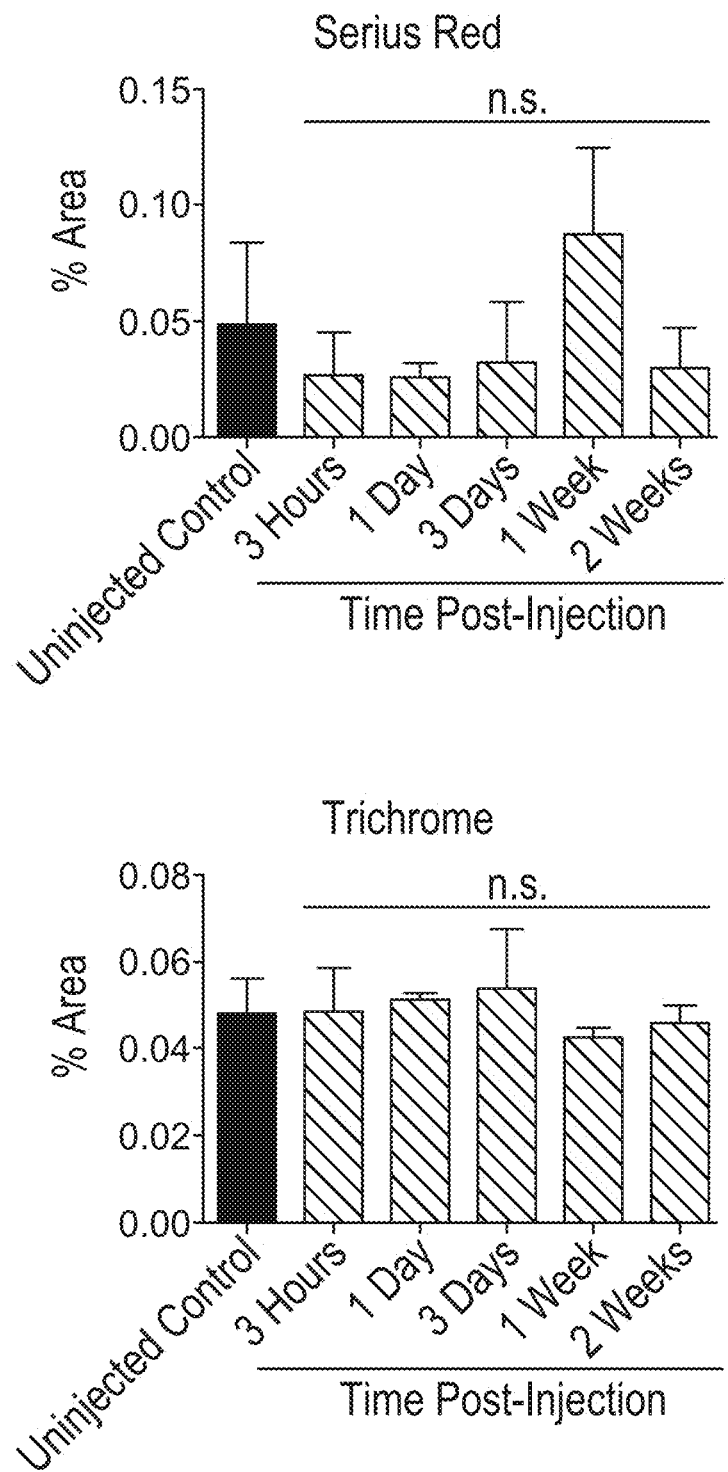

Increase in pancreatic intraductal pressure is known to cause inflammation/pancreatitis, a known risk factor for PDAC, and impact experimental outcomes. To evaluate the effect of intraductal delivery mediated pressure on pancreatic inflammation, a cohort of C57BL/6 mice was dosed with PBS and monitored serum pancreatitis markers, amylase and lipase. A rapid increase in amylase and lipase levels were observed at 3 hours post-vector delivery which resolved within a day of intraductal infusion (FIGS. 12A & 12B). By histopathological examination, there was minimal to no pancreatic inflammation seen at various time points (FIG. 12C), except for a detectable peri-pancreatic fat lymphoid response in a few mice at 2-5 days post-injection (FIG. 13D). Pancreata was also stained with the B cell marker (B220) to monitor lymphoid responses. Normal mice were negative for B220 at all time points, 1-15 days post-injection (FIG. 12C). In addition, to evaluate the effect of intraductal mediated pressure on pancreatic fibrosis, pancreata of C57BL/6 mice were stained with trichrome (FIG. 12D) and found no significant increase in pancreatic fibrosis in intraductally dosed mice compared to non-injected control mice FIG. 12E).

Figure 13A:
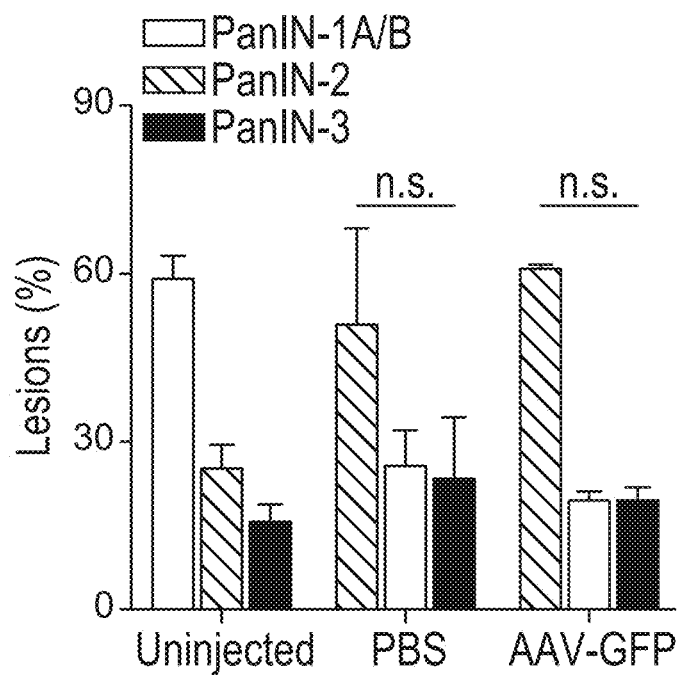
FIGS. 13A & 13B: retrograde pancreatic intraductal delivery has no effect on PDAC progression in KC mice. Pancreata collected from KC mice at 5-months post-infusion (100 ul of PBS or 5×10¹¹ vg scAAV6.GFP) was analyzed and compared against un-injected control mice for (FIG. 13A) PanIN grades (1A/B, 2 & 3) by histopathological analysis of H&E, and (FIG. 13B) Trichrome staining positive percentage area was quantified (n=3-5/group). Mean±S.E.M, t-test. n.s.: non-significant.
Figure 13B:
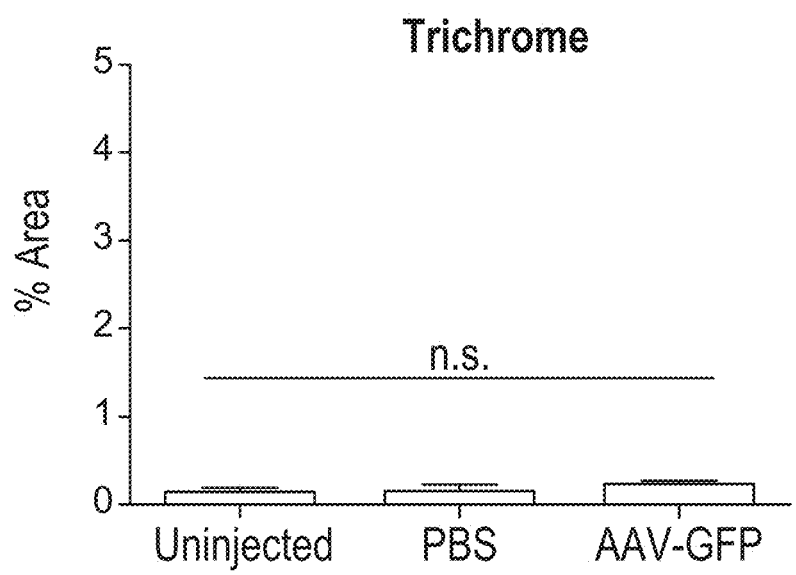

Finally, to evaluate the effect of intraductal delivery mediated inflammation on PDAC progression, histopathological analysis was performed in KC mice dosed with PBS or scAAV6.GFP at 5 months post-infusion. As shown in FIG. 13A, there was no significant difference in PanIN grades between intraductally injected KC mice compared to un-injected controls. Furthermore, intraductually infused KC mice were negative for B220 staining <1%, and there was no significant increase in pancreatic fibrosis quantified based on trichrome staining (FIG. 13B).

In summary, among various vector systems and routes of administration, retrograde ductal delivery of AAV demonstrated efficient pancreatic gene expression. This Example further shows that AAV could be used as a delivery vehicle for genome editing tools for functional studies. For example, the retrograde ductal delivery method will be particularly useful in studying the gene function of non-coding RNAs, such as miRNAs. Particularly, delivering synthetic miRNA duplexes, for example, miRNA29 and mimics thereof, would be beneficial, and evidence suggests the use of AAV for provide in vivo delivery of therapeutic miRNA with no toxicity.

What is claimed is:

1. A method of inhibiting cancer cell migration in a subject in need thereof, the method comprising administering to the subject at least one miR-29 mimic and increasing expression levels of miR-29 in the cancer cells in the subject, wherein the cancer cells are pancreatic cancer cells.

2. The method of claim 1, wherein the at least one miR-29 mimic is selected from the group consisting of: miR-29a mimic, miR-29b mimic, miR-29c mimic and any combination thereof.

3. The method of claim 1 further comprising administering to the subject a chemotherapeutic agent.

4. The method as set forth in claim 3, wherein the chemotherapeutic agent is selected from the group consisting of: gemcitabine, nab-paclitaxel, FOLFIRINOX, and combinations thereof.

5. The method of claim 1, wherein the at least one miR-29 mimic is administered by: transient transfection, a viral vector, encapsulation, liposomal nanoparticles, and any combination thereof.

6. The method of claim 5, wherein the viral vector is adeno-associated virus or lentivirus.

7. The method of claim 1, wherein the route of administration of the at least one miR-29 mimic is selected from: intravenous delivery, intraductal delivery, intratumoral delivery, and any combination thereof.

8. The method of claim 1, wherein the at least one miR-29 mimic is administered between a concentration of about 10 nM to about 20 nM.

9. The method of claim 1, wherein the subject has pancreatic cancer.

* * * * *